United States Patent
Beck et al.

(10) Patent No.: US 9,695,094 B2
(45) Date of Patent: *Jul. 4, 2017

(54) PRODUCTION OF AROMATICS FROM DI- AND POLYOXYGENATES

(71) Applicant: Virent, Inc., Madison, WI (US)

(72) Inventors: Taylor Beck, Madison, WI (US); Brian Blank, Monona, WI (US); Casey Jones, Madison, WI (US); Elizabeth Woods, Middleton, WI (US); Randy Cortright, Madison, WI (US)

(73) Assignee: Virent, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/217,715

(22) Filed: Jul. 22, 2016

(65) Prior Publication Data

US 2016/0332941 A1 Nov. 17, 2016

Related U.S. Application Data

(62) Division of application No. 14/211,795, filed on Mar. 14, 2014, now Pat. No. 9,403,736.

(Continued)

(51) Int. Cl.
  *C07D 321/00* (2006.01)
  *C07C 1/00* (2006.01)
  (Continued)

(52) U.S. Cl.
  CPC ............. *C07B 35/06* (2013.01); *B01J 21/066* (2013.01); *B01J 23/14* (2013.01); *B01J 23/6527* (2013.01); *B01J 23/755* (2013.01); *B01J 23/835* (2013.01); *B01J 23/888* (2013.01); *B01J 29/46* (2013.01); *B01J 29/90* (2013.01); *B01J 37/0201* (2013.01);
  (Continued)

(58) Field of Classification Search
  CPC . C07C 1/20; C07C 1/24; C07C 1/2072; B01J 21/066; B01J 23/14; B01J 23/6527; B01J 23/835; B01J 23/888; B01J 29/46; B01J 29/90; B01J 37/0201; B01J 37/0213; B01J 38/02; B01J 38/12
  USPC ........ 585/469, 733, 408, 322, 321; 549/200; 568/303
  See application file for complete search history.

(56) References Cited

U.S. PATENT DOCUMENTS 9,440,892 B2 * 9/2016 Beck .......................... C07C 1/24

OTHER PUBLICATIONS

Zhang et al, Catalytic Conversion of Biomass-Derived Feedstocks into Olefins and Aromatics with ZSM-5: the hydrogen to carbon effective ratio, Energy Environ. Sci. 2011, 4, 229-2307.*

* cited by examiner

*Primary Examiner* — T. Victor Oh
(74) *Attorney, Agent, or Firm* — Quarles & Brady LLP

(57) ABSTRACT

Methods, catalysts, and reactor systems for producing in high yield aromatic chemicals and liquid fuels from a mixture of oxygenates comprising di- and polyoxygenates are disclosed. Also disclosed are methods, catalysts, and reactor systems for producing aromatic chemicals and liquid fuels from oxygenated hydrocarbons such as carbohydrates, sugars, sugar alcohols, sugar degradation products, and the like; and methods, catalysts, and reactor systems for producing the mixture of oxygenates from oxygenated hydrocarbons such as carbohydrates, sugars, sugar alcohols, sugar degradation products, and the like. The disclosed catalysts for preparing the mixture of oxygenates comprise a $Ni_nSn_m$ alloy and a crystalline alumina support.

13 Claims, 13 Drawing Sheets

Related U.S. Application Data

(60) Provisional application No. 61/784,417, filed on Mar. 14, 2013.

(51) Int. Cl.

| | | |
|---|---|---|
| *C07C 49/00* | (2006.01) | |
| *C07C 27/10* | (2006.01) | |
| *C07B 35/06* | (2006.01) | |
| *C07C 1/24* | (2006.01) | |
| *B01J 23/835* | (2006.01) | |
| *C07C 1/207* | (2006.01) | |
| *C07C 29/60* | (2006.01) | |
| *C07D 301/02* | (2006.01) | |
| *B01J 23/14* | (2006.01) | |
| *C10G 3/00* | (2006.01) | |
| *B01J 38/02* | (2006.01) | |
| *B01J 38/12* | (2006.01) | |
| *B01J 21/06* | (2006.01) | |
| *B01J 23/652* | (2006.01) | |
| *B01J 23/888* | (2006.01) | |
| *B01J 29/46* | (2006.01) | |
| *B01J 29/90* | (2006.01) | |
| *B01J 37/02* | (2006.01) | |
| *C07C 45/00* | (2006.01) | |
| *C07C 51/377* | (2006.01) | |
| *B01J 23/755* | (2006.01) | |

(52) U.S. Cl.
CPC ............ *B01J 37/0213* (2013.01); *B01J 38/02* (2013.01); *B01J 38/12* (2013.01); *C07C 1/2072* (2013.01); *C07C 1/24* (2013.01); *C07C 29/60* (2013.01); *C07C 45/002* (2013.01); *C07C 51/377* (2013.01); *C07D 301/02* (2013.01); *C10G 3/46* (2013.01); *C10G 3/47* (2013.01); *C10G 3/48* (2013.01); *C10G 3/49* (2013.01); *C10G 3/50* (2013.01); *C10G 2300/1014* (2013.01); *C10G 2400/30* (2013.01); *Y02P 20/584* (2015.11); *Y02P 20/588* (2015.11); *Y02P 30/20* (2015.11)

PRODUCTION OF AROMATICS FROM DI- AND POLYOXYGENATES

CROSS-REFERENCE TO RELATED APPLICATIONS

This application is a divisional of U.S. patent application Ser. No. 14/211,795, filed Mar. 14, 2014, issued on Aug. 2, 2016 as U.S. Pat. No. 9,403,736, which claims the benefit of U.S. provisional Application No. 61/784,417 filed on Mar. 14, 2013, each of which is incorporated by reference herein in its entirety.

FEDERALLY SPONSORED RESEARCH OR DEVELOPMENT

This invention was made with government support under an award provided by the U.S. Department of Energy, Award Nos. DE-EE0003044 and DE-EE0005006. The government has certain rights in the invention.

BACKGROUND OF THE INVENTION

Previous efforts for converting biomass to liquid fuels and chemicals have focused on transforming a variety of oxygenated hydrocarbons to desirable products using condensation reaction pathways. The condensation reaction can be catalyzed using a zeolite catalyst, for example, under moderate conditions (i.e. temperatures between 80° C. and 600° C. and pressures at or slightly greater than atmospheric).

The most common process for converting oxygenated hydrocarbons to gasoline range hydrocarbons is known as the methanol to gasoline (MTG) process (Mobil Oil Corporation ca. 1980). Additionally, Mobil and ConocoPhillips have developed and patented methods for converting biomass derived carbohydrates (e.g., glucose, xylose, starch, sucrose) and sugar alcohols (sorbitol and xylitol) to similar gasoline range hydrocarbons. However, one of the major disadvantages of processing these highly oxygenated species with zeolite catalysts is the production of high yields of undesired coke, which severely harm/limit catalyst performance and final product yields.

Chen et al. developed the hydrogen to carbon effective (H:$C_{eff}$) ratio as a tool to assist in determining the suitability of oxygenated hydrocarbon feedstocks for catalytic conversion to hydrocarbons using zeolite catalysts (N. Y. Chen, J. T. F. Degnan and L. R. Koenig, *Chem. Tech.* 1986, 16, 506). The H:$C_{eff}$ ratio is based on the amount of carbon, oxygen and hydrogen in the feed, and is calculated as follows:

$$H: C_{eff} = \frac{H - 2O}{C}$$

where H represents the number of hydrogen atoms, O represents the number of oxygen atoms, and C represents the number of carbon atoms. Water and molecular hydrogen (diatomic hydrogen, $H_2$) are excluded from the calculation. The H:$C_{eff}$ ratio applies both to individual components and to mixtures of components, but is not valid for components which contain atoms other than carbon, hydrogen, and oxygen. For mixtures, the C, H, and O are summed over all components exclusive of water and molecular hydrogen. The term "hydrogen" refers to any hydrogen atom, while the term "molecular hydrogen" is limited to diatomic hydrogen, $H_2$.

Zhang et al. studied the impact of the H:$C_{eff}$ ratio on the conversion of various biomass-derived oxygenated hydrocarbons to coke, olefins and aromatics using a ZSM-5 catalyst (Zhang et al., *Catalytic conversion of biomass-derived feedstocks into olefins and aromatics with ZSM-5: the hydrogen to carbon effective ratio*, Energy Environ. Sci., 2011, 4, 2297). Zhang reported that biomass derived feedstocks having H:$C_{eff}$ ratios of between 0 and 0.3 produced high levels of coke, making it non-economical to convert such feedstocks to aromatics and chemicals. By hydroprocessing the feedstock to add hydrogen, Zhang was able to produce aromatics and olefins using a ZSM-5 catalyst at yields higher than a process without hydrogenation. However, the ratio of olefins to aromatics also increased with increasing H:$C_{eff}$ ratio, with the olefin yield higher than the yield of aromatics for all feedstocks. It was reported that there is also an inflection point at a H:$C_{eff}$ ratio of 1.2, where the aromatic and olefin yield does not increase further. Zhang indicated that at most the yield of high value aromatic chemicals, such as benzene, toluene, and xylenes (BTX), may be limited to 24% when using zeolite catalysts according to the disclosed process.

Oxygenated hydrocarbons derived from biomass, such as carbohydrates, sugars, and sugar alcohols have a low H:$C_{eff}$ ratio. A typical carbohydrate or sugar has a formula that can be represented by the formula $((CH_2O)_n)_m$ where n is typically equal to 3-6 (i.e. triose, tetrose, pentose, or hexose) and m is any number between 1 (i.e. a monosaccharide) and tens of thousands for large polysaccharides. A molecule of the formula $((CH_2O)_n)_m$ will have a H:$C_{eff}$ ratio of 0. Sugar alcohols, likewise, have low H:$C_{eff}$ ratios. For example, the $C_6$ and $C_5$ sugar alcohols like sorbitol and xylitol have an H:$C_{eff}$ of 0.33 and 0.4, respectively, making them undesirable for condensation reactions due to the excessive amount of coke formed on the condensation catalyst.

To overcome the limitations in converting oxygen-rich (alternatively, hydrogen-deficient) biomass-derived feedstocks to hydrocarbons, biomass derived feedstocks have been converted to oxygen-deficient (alternatively, hydrogen-rich) molecules, such as monooxygenated hydrocarbons (alcohols, ketones, cyclic ethers, etc.), while keeping the carbon chain intact. The monooxygenates are subsequently converted to gasoline range hydrocarbons using a condensation catalyst. See, for example, U.S. Pat. Nos. 7,767,867, 8,017,818, 8,231,857 and U.S. patent application Ser. Nos. 12/980,892 and 13/586,499, the contents of which are incorporated herein in their entirety.

Under the described methods, the conversion to monooxygenates from the biomass-derived oxygenated hydrocarbons results in an oxygenate mixture having an overall H:$C_{eff}$ ratio close to 2. The overall H:$C_{eff}$ ratio is based on the combined H:$C_{eff}$ ratio for all of the hydrocarbons (both oxygenated and non-oxygenated) in the oxygenate mixture. The monohydroxyl alcohols have a H:$C_{eff}$ ratio of 2.0 regardless of size, while the H:$C_{eff}$ ratio for cyclic ethers, ketones, aldehydes, and alkanes vary with the length of the hydrocarbon. For example, the H:$C_{eff}$ for the $C_6$ and $C_5$ cyclic ethers, ketones, and aldehydes is 1.67 and 1.6, respectively, while the H:$C_{eff}$ for the $C_6$ and $C_5$ alkanes is 2.33 and 2.40, respectively. The alkanes in any substantial quantity are particularly undesirable because they are largely unreactive when further processed during condensation and contribute to a higher H:$C_{eff}$ ratio.

Although forming monooxygenates allows for the condensation of oxygenates without the production of an excessive amount of coke on the catalyst, the process comes at a cost. Specifically, condensation of monooxygenates leads to substantial alkane production often at yields comparable to the production of aromatic molecules. For applications where aromatic molecules are highly desirable, the significant production of alkanes reduces the total aromatics produced, thereby increasing the overall cost of the final end products. Therefore, there is a need for methods for yielding aromatics in high percentages while minimizing alkane production, methods for producing the mixture of oxygenates useful for those methods, and the catalysts used in the methods for forming the mixture of oxygenates. In addition, there is a need for the methods to also have a low coke yield.

The inventors have surprisingly found solutions for all of those needs based on refinements made to the overall oxygenate mixture. In particular, the inventors have discovered that a mixture of oxygenates having a H:$C_{eff}$ ratio in the range of 0.5 to 1.7 and one or more of the following attributes provides unexpected and beneficial results to improving aromatics production: (1) more di- and polyoxygenates than monooxygenates, (2) more dioxygenates than monooxygenates, (3) more $C_{2-4}$ oxygenates (especially di- and polyoxygenates) than $C_{5-6}$ oxygenates (especially monooxygenates), and/or (4) little to no alkanes present.

SUMMARY

The invention provides methods for making biomass-derived chemicals and fuels with a high yield of aromatic molecules and a low yield of alkanes. The invention also provides methods for making a mixture of oxygenates from biomass that react in the presence of a condensation catalyst to produce chemicals and fuels with a high yield of aromatic molecules and a low yield of alkanes. In addition, the invention also provides catalysts useful in the production of the mixture of oxygenates capable of being reacted to produce a high yield of aromatic molecules and a low yield of alkanes. An additional aspect of the invention is that the methods produce a low yield of coke when making aromatic molecules.

An embodiment of the invention is a catalyst composition capable of producing a mixture of oxygenates which can be reacted to produce hydrocarbons having a high yield of aryls and a low yield of alkanes, the catalyst composition comprising a $Ni_nSn_m$ alloy and a crystalline alumina support. In certain embodiments, n equals 3 and m equals 1 or 2. In certain embodiments, the wt % of Ni may be greater than or equal to 0.5 wt %, greater than or equal to 1.0 wt % or greater than or equal to 2.0%. In certain embodiments the wt % of Ni may be less than or equal to 20%, less than or equal to 15% less than or equal to 12 wt %, or less than or equal to 10 wt %. In certain embodiments, the crystalline alumina support may be a transitional alumina support. In certain embodiments, the crystalline alumina support may be a theta-alumina support. In certain embodiments, the crystalline alumina support may be modified with a member selected from the group consisting of B, Cr, Ce, Co, Cu, Fe, Mg, Mo, Nb, W, Zr, and mixtures thereof. Certain embodiments may include a composition of matter useful for producing hydrocarbons having a high yield of aryls and a low yield of alkanes by reacting an aqueous feedstock, the catalyst composition comprising a $Ni_nSn_m$ alloy and a crystalline alumina support, oxygenated hydrocarbons, and a mixture of oxygenates.

In another embodiment, the $Ni_nSn_m$ alloy and a crystalline alumina support may be useful for reacting an aqueous feedstock, the aqueous feedstock comprising water and one or more oxygenated hydrocarbons selected from the group consisting of monosaccharides, disaccharides, oligosaccharides, polysaccharides, sugar alcohols, sugar degradation products, cellulosic derivatives, hemicellulosic derivatives, lignin derivatives, lignocellulosic derivatives, and mixtures thereof, with hydrogen in the presence of the catalyst to produce a mixture of oxygenates, wherein the H:$C_{eff}$ ratio of the mixture of oxygenates is greater than or equal to 0.5 and less than or equal to 1.7.

In another embodiment, the $Ni_nSn_m$ alloy and a crystalline alumina support may be useful for reacting an aqueous feedstock, the aqueous feedstock comprising water and one or more oxygenated hydrocarbons selected from the group consisting of monosaccharides, disaccharides, oligosaccharides, polysaccharides, sugar alcohols, sugar degradation products, cellulosic derivatives, hemicellulosic derivatives, lignin derivatives, lignocellulosic derivatives, and mixtures thereof, with hydrogen in the presence of the catalyst to produce a mixture of oxygenates and reacting the mixture of oxygenates with a condensation catalyst to produce a mixture of hydrocarbons comprising $C_{4+}$ alkanes and aryls, wherein the mixture of hydrocarbons comprises greater than or equal to 50% CF aryls and less than or equal to 20% CF $C_{4+}$ alkanes. In certain embodiments, the mixture of hydrocarbons comprises greater than or equal to 55% CF aryls, greater than or equal to 60% CF aryls, or greater than or equal to 65% CF aryls. In certain embodiments, the mixture of hydrocarbon comprises less than or equal to 15% CF $C_{4+}$ alkanes, less than or equal to 10% CF $C_{4+}$ alkanes, or less than or equal to 5% CF $C_{4+}$ alkanes. In any of the embodiments above, the aryls may comprise one or more aryls selected from the group consisting of benzene, toluene, xylene, paraxylene, metaxylene, orthoxylene, and ethylbenzene.

In any of the embodiments above, the mixture of oxygenates may have one or more attributes selected from the group consisting of (i) a % CF ratio greater than or equal to 0.5 of dioxygenates and polyoxygenates to monooxygenates, (ii) a % CF ratio greater than or equal to 0.5 of dioxygenates to monooxygenates, (iii) a % CF ratio greater than or equal to 1.0 of $C_{2-4}$ oxygenates to $C_{5-6}$ oxygenates, and (iv) the mixture of oxygenates further comprising less than or equal to 10% CF alkanes.

In any of the embodiments above, the H:$C_{eff}$ ratio of the mixture of oxygenates may be less than or equal to 1.6, less than or equal to 1.5, or less than or equal to 1.4. In certain embodiments, the H:$C_{eff}$ ratio of the mixture of oxygenates may be greater than or equal to 0.6, greater than or equal to 0.7, greater than or equal to 0.8, greater than or equal to 0.9, or greater than or equal to 1.0.

In any of the embodiments above, the mixture of oxygenates may comprise greater than or equal to about 30% CF dioxygenates and polyoxygenates, greater than or equal to 40% CF dioxygenates and polyoxygenates, greater than or equal to 50% CF dioxygenates and polyoxygenates, or greater than or equal to 60% CF dioxygenates and polyoxygenates. In certain embodiments, the mixture of oxygenates may comprise greater than or equal to 30% CF dioxygenates, greater than or equal to 40% CF dioxygenates, greater than or equal to 50% CF dioxygenates, or greater than or equal to 60% CF dioxygenates. In certain embodiments, the mixture of oxygenates may comprise greater than or equal to 20% CF diols, greater than or equal to 30% CF diols, greater than or equal to 40% CF diols, or greater than or equal to 50% CF diols.

DETAILED DESCRIPTION

Figure 1:
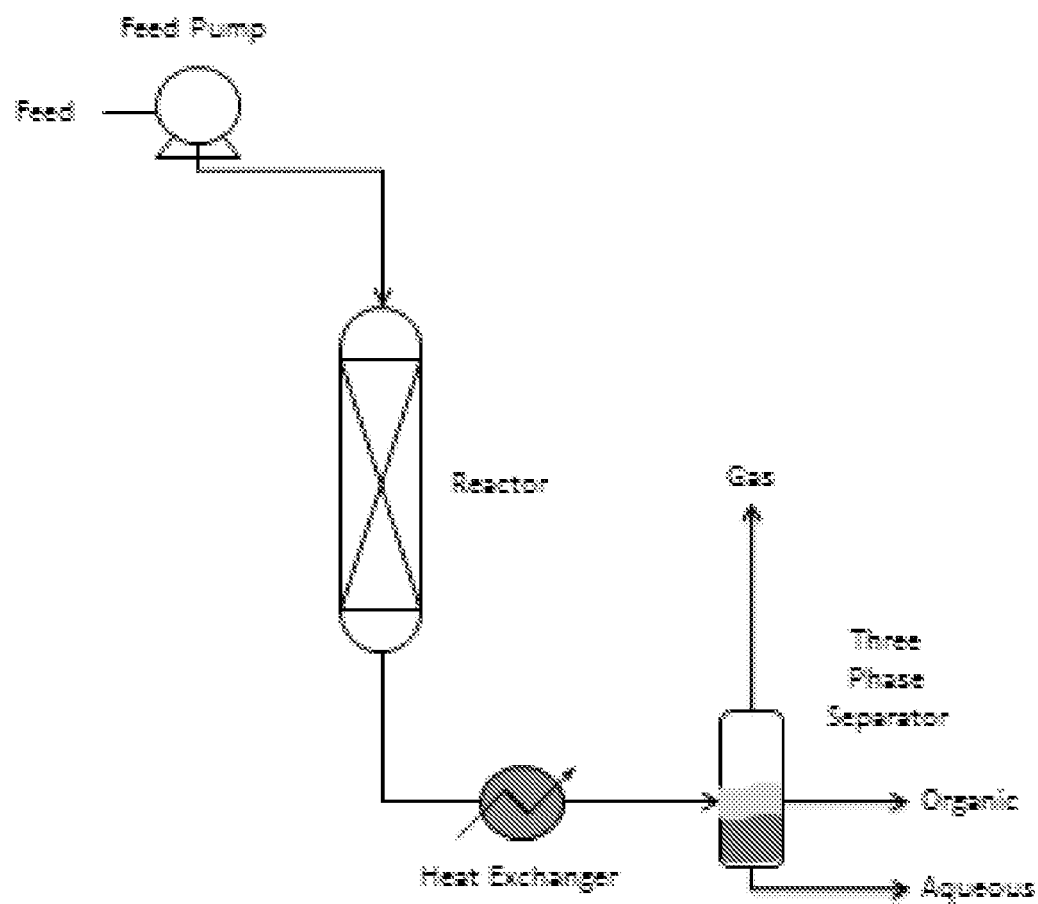
FIG. 1 is an exemplary flow diagram for converting oxygenated hydrocarbons to oxygenated compounds or for converting oxygenated compounds to hydrocarbons.

The invention generally provides for processes for making biomass-derived chemicals and fuels with a high yield of aromatic molecules and a low yield of alkanes and coke. Surprisingly, the present method allows for the production of a mixture of hydrocarbons having greater than or equal to 50% aromatic molecules, while also having less than or equal to 20% alkanes.

The invention also provides methods for making a mixture of oxygenates from biomass that react in the presence of a condensation catalyst to produce chemicals and fuels with a high yield of aromatic molecules and a low yield of alkanes. Additionally, the invention also results in a low yield of coke when producing aromatic chemicals. The mixture of oxygenates will generally have a $H:C_{eff}$ ratio of greater than or equal to 0.5 to less than or equal to 1.7, which allows for the surprisingly high yield of aromatic molecules while minimizing the yield of alkanes. The mixture of oxygenates may also have one or more of the following attributes: (1) more di- and polyoxygenates than monooxygenates, (2) more dioxygenates than monooxygenates, (3) more $C_{2-4}$ oxygenates (especially di- and polyoxygenates) than $C_{5-6}$ oxygenates (especially monooxygenates), and/or (4) little to no alkanes present.

The mixture of oxygenates may originate from any source, but may also be produced by reacting an aqueous feedstock solution containing a water-soluble oxygenated hydrocarbon having three or more carbon atoms with hydrogen over a deoxygenation catalyst to produce the desired oxygenate mixture. The mixture of oxygenates are then reacted over a condensation catalyst under conditions of temperature and pressure effective to cause a condensation reaction that produces the high yield of aromatic molecules and a low yield of alkanes and coke. The oxygenated hydrocarbon may be a monosaccharide, disaccharide, polysaccharide, cellulose, hemicellulose, lignin, sugar, sugar alcohol or other polyhydric alcohols, sugar degradation products, or may be derived from the hydrogenation of a sugar, furfural, carboxylic acid, ketone, or furan, or the hydrogenolysis of a sugar, sugar alcohol, polysaccharide, monosaccharide, disaccharide or polyhydric alcohol. The invention also provides for the deoxygenation catalyst useful for producing the mixture of oxygenates.

One aspect of the invention is the production of a hydrocarbon stream having a high yield of aromatic molecules and a low yield of alkanes. In particular, the method provides for an aryl yield greater than or equal to 50% CF and $C_{4+}$ alkane yield less than or equal to 20% CF. In certain embodiments the aryls yield can be greater than or equal to 55% CF, greater than or equal to 60% CF, or greater than or equal to 65% CF. In certain embodiments, the $C_{4+}$ alkane yield is less than or equal to 15% CF, less than or equal to 10% CF, or less than equal to 5% CF. In certain other embodiments, the product may further comprise $C_{1-3}$ alkanes with the total $C_{1+}$ alkane yield less than or equal to 20% CF, less than or equal to 15% CF, less than or equal to 10% CF, or less than or equal to 5% CF. The % CF is calculated by dividing the mass of carbon of the component (e.g. mass of carbon in the aryls) by the mass of carbon in the feed and multiplying by 100. Alternatively, the % CF may be reported as percentage of feed carbon, percentage of carbon in, or other similar nomenclature.

In certain embodiments, the aryls yield is greater than or equal to 55% CF and the $C_{4+}$ alkane yield is less than or equal to 15% CF. In another embodiment the aryls yield is greater than or equal to 60% CF and the $C_{4+}$ alkane yield is less than or equal to 10% CF. In further embodiments, the aryls yield is greater than or equal to 55% CF and the $C_{1+}$ alkane yield is less than or equal to 15% CF. In yet other embodiments, the aryls yield is greater than or equal to 60% CF and the $C_{4+}$ alkane yield is less than or equal to 10% CF.

One aspect of the invention that allows for the surprising benefit of high aromatic hydrocarbon yield and low alkane and are the mixtures of oxygenates feed into the condensation reactor. In addition the invention allows for the surprising benefit of low coke yield on the condensation catalyst. Typical biomass-derived oxygenated hydrocarbons from sugars, starches, hemicellulose, cellulose and the like have very low $H:C_{eff}$ ratios around 0.0. Because these biomass-derived compounds are so oxygen-rich (conversely, hydrogen-poor) they tend to coke-up condensation catalyst. Monooxygenates on the other hand have a much higher $H:C_{eff}$ ($H:C_{eff}$ equals 2.0 for alcohols), and tend to result in substantial alkane production, often at yields comparable to the desired aromatic molecules. An ideal mixture to produce a high yield of aromatic molecules, while minimizing the amount of alkanes produced will have a $H:C_{eff}$ ratio between 0.5 and 1.7. By way of comparison, oxygenated compounds that are well suited for producing high yields of aromatics and low yields of alkanes have 2 to 4 carbon atoms and 2 or 3 oxygen atoms. The $H:C_{eff}$ ratios for these molecules are generally between 0.5 and 1.5. Examples include $C_{2-4}$ diols and triols, such as ethylene glycol with a $H:C_{eff}$ of 1, propylene glycol with a $H:C_{eff}$ of 1.33, glycerol with a $H:C_{eff}$ of 0.67, butanediol with a $H:C_{eff}$ of 1.25, and butantriol with a $H:C_{eff}$ of 1. Smaller di- and/or polyoxygenates, such as $C_{2-4}$ compounds having carboxylic acid, hydroxyketone, or hydroxyaldehyde moieties and RCOOR' esters (where R is $C_{1-3}$ and R' is $C_{1-4}$) may also fall within the desired $H:C_{eff}$ range.

Without being bound to any particular theory, the inventors believe that hydrogen atoms, made available through the conversion of relatively hydrogen-deficient biomass-derived feedstocks to $C_{2-4}O_{2-3}$ oxygenates allows reaction pathways to be exploited across the condensation catalyst that are not otherwise feasible. The reaction pathways include reactions that can directly lead to olefin intermediates. Additional olefin intermediates may be indirectly generated through the release and transfer of hydrogen as aromatics are formed, with the hydrogen released by the formation of the aromatics transferred to unsaturated oxygenates such as esters, ketones, aldehydes, carboxylic acids or other oxygenated molecules such as diols, or polyols. As used herein, oxygenates capable of reacting with hydrogen in this manner are termed "hydrogen acceptors". It is believed that carbonyls, carboxylic acids, esters, cyclic ethers, diols, polyols, furans and other oxygenates characterized by having a $H:C_{eff}$ ratio of less than 2 are capable of being hydrogen acceptors, either directly or following other reactions (such as dehydration), which have converted the components to hydrogen acceptors. After accepting hydrogen, the hydrogen acceptors may be converted into species that readily dehydrate to form olefins or may be capable of accepting further hydrogen.

Generally, the mixture of oxygenates will have a $H:C_{eff}$ ratio greater than or equal to 0.5 and less than or equal to 1.7, and one or more of the following attributes: (1) more di- and polyoxygenates than monooxygenates, (2) more dioxygenates than monooxygenates, (3) more $C_{2-4}$ oxygenates (especially di- and polyoxygenates) than $C_{5-6}$ oxygenates (especially monooxygenates), and/or (4) little to no alkanes present.

In most embodiments, the mixture of oxygenates will have a $H:C_{eff}$ ratio greater than or equal to 0.5, greater than or equal to 0.6, greater than or equal to 0.7, greater than or equal to 0.8, greater than or equal to 0.9, or greater than or equal to 1.0. The mixture of oxygenates also has a $H:C_{eff}$ ratio less than or equal to 1.7, less than or equal to 1.6, less than or equal to 1.5, or less than or equal to 1.4.

The mixture of oxygenates will also generally have a substantial amount of dioxygenates and/or polyoxygenates. In such embodiments, the oxygenate mixtures may have greater than or equal to 30% CF dioxygenates and polyoxygenates, greater than or equal to 35% CF dioxygenates and polyoxygenates, greater than or equal to 40% CF dioxygenates and polyoxygenates, greater than or equal to 45% CF dioxygenates and polyoxygenates, greater than or equal to 50% CF dioxygenates and polyoxygenates, greater than or equal to 55% CF dioxygenates and polyoxygenates, greater than or equal to 60% CF dioxygenates and polyoxygenates, greater than or equal to 65% CF dioxygenates and polyoxygenates, greater than or equal to 70% CF dioxygenates and polyoxygenates, greater than or equal to 75% CF dioxygenates and polyoxygenates, greater than or equal to 80% CF dioxygenates and polyoxygenates, greater than or equal to 85% CF dioxygenates and polyoxygenates, greater than or equal to 90% CF dioxygenates and polyoxygenates, or any % CF between any interval thereof. In this instance, the % CF is calculated by dividing the mass of carbon of the components (e.g. mass of carbon in the di- and polyoxygenates molecules) by the mass of carbon in the mixture of oxygenates and multiplying by 100.

In other embodiments, the mixture of oxygenates may have greater than or equal to 30% CF dioxygenates, greater than or equal to 35% CF dioxygenates, greater than or equal to 40% CF dioxygenates, greater than or equal to 45% CF dioxygenates, greater than or equal to 50% CF dioxygenates, greater than or equal to 55% CF dioxygenates, greater than or equal to 60% CF dioxygenates, greater than or equal to 65% CF dioxygenates, greater than or equal to 70% CF dioxygenates, greater than or equal to 75% CF dioxygenates, greater than or equal to 80% CF dioxygenates, greater than or equal to 85% CF dioxygenates, greater than or equal to 90% CF dioxygenates, or any % CF between any interval thereof. In this instance, the % CF is calculated by dividing the mass of carbon of the components (e.g. mass of carbon in the dioxygenates molecules) by the mass of carbon in the mixture of oxygenates and multiplying by 100.

In other embodiments, the mixture of oxygenates may have greater than or equal to 20% CF diols, greater than or equal to 25% CF diols, greater than or equal to 30% CF diols, greater than or equal to 35% CF diols, greater than or equal to 40% CF diols, greater than or equal to 45% CF diols, greater than or equal to 50% CF diols, greater than or equal to 55% CF diols, greater than or equal to 60% CF diols, greater than or equal to 65% CF diols, greater than or equal to 70% CF diols, greater than or equal to 75% CF diols, greater than or equal to 80% CF diols, or any % CF between any interval thereof. In this instance, the % CF is calculated by dividing the mass of carbon of the components (e.g. mass of carbon in the diol molecules) by the mass of carbon in the mixture of oxygenates and multiplying by 100.

In other embodiments, the mixture of oxygenates may have less than or equal to 20% CF monoxygenates, less than or equal to 15% CF monoxygenates, less than or equal to 10% CF monoxygenates, less than or equal to 9% CF monoxygenates, less than or equal to 8% CF monoxygenates, less than or equal to 7% CF monoxygenates, less than or equal to 5% CF monoxygenates, less than or equal to 5% CF monoxygenates, less than or equal to 5% CF monoxygenates, less than or equal to 4% CF monoxygenates, less than or equal to 3% CF monoxygenates, less than or equal to 2% CF monoxygenates, less than or equal to 1% CF monoxygenates, or any % CF between any interval thereof. In this instance, the % CF is calculated by dividing the mass of carbon of the components (e.g. mass of carbon in the monooxygenates) by the mass of carbon in the mixture of oxygenates and multiplying by 100.

In other embodiments, the mixture of oxygenates may have less than or equal to 20% CF alcohols, less than or equal to 15% CF alcohols, less than or equal to 10% CF alcohols, less than or equal to 9% CF monoxygenates, less than or equal to 8% CF alcohols, less than or equal to 7% CF alcohols, less than or equal to 5% CF alcohols, less than or equal to 5% CF alcohols, less than or equal to 4% CF alcohols, less than or equal to 3% CF alcohols, less than or equal to 2% CF alcohols, less than or equal to 1% CF alcohols, or any % CF between any interval thereof. In this instance, the % CF is calculated by dividing the mass of carbon of the components (e.g. mass of carbon in the alcohols) by the mass of carbon in the mixture of oxygenates and multiplying by 100.

A first possible attribute of the mixture of oxygenates is that the % CF ratio of di- and polyoxygenates to monooxygenates is greater than or equal to 0.5, where the % CF ratio is calculated by dividing the % CF for each component (i.e. % CF dioxygenates and polyoxygenates divided by % CF monooxygenates). In certain embodiments, the % CF ratio of di- and polyoxygenates to monooxygenates is greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 3.0, greater than or equal to 4.0, greater than or equal to 5.0, greater than or equal to 6.0, greater than or equal to 7.0, greater than or equal to 8.0, greater than or equal to 9.0, greater than or equal to 10.0, greater than or equal to 11.0, greater than or equal to 12.0, greater than or equal to 13.0, greater than or equal to 14.0, greater than or equal to 15.0, greater than or equal to 20.0, greater than or equal to 25.0, greater than or equal to 35.0, greater than or equal to 45.0, or any ratio in between any interval thereof. The % CF ratio of dioxygenates and polyoxygenates to monooxygenates can also more easily be measured by the ratio of diols and triols to alcohols in certain embodiments.

A second possible attribute of the mixture of oxygenates is that the % CF ratio of dioxygenates to monooxygenates is greater than or equal to 0.5, where the % CF ratio is calculated by dividing the % CF for each component (i.e. % CF dioxygenates divided by % CF monooxygenates). In certain embodiments, the % CF ratio of dioxygenates to monooxygenates is greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 3.0, greater than or equal to 4.0, greater than or equal to 5.0, greater than or equal to 6.0, greater than or equal to 7.0, greater than or equal to 8.0, greater than or equal to 9.0, greater than or equal to 10.0, greater than or equal to 11.0, greater than or equal to 12.0, greater than or equal to 13.0, greater than or equal to 14.0, greater than or equal to 15.0, greater than or equal to 20.0, greater than or equal to 25.0, greater than or equal to 35.0, greater than or equal to 45.0, or any ratio in between any interval thereof. The % CF ratio of dioxygenates to monooxygenates can also more easily be measured by the ratio of diols to alcohols. As shown in Example 1, this leads to a surprising and unexpected ability of the mixture of oxygenates to produce greater quantities of aromatic molecules while minimizing the production of undesired alkanes as the ratio of the diol to alcohol increases. At the largest ratio presented, the condensation reaction surprisingly resulted in greater than or equal to 65CF % aromatics and less than or equal to 10CF % paraffins.

A third possible attribute of the mixture of oxygenates is that the % CF ratio of $C_{2-4}$ oxygenates to $C_{5-6}$ oxygenates is greater than or equal to 1.0, where the % CF ratio is calculated by dividing the % CF for each component (i.e. % CF $C_{2-4}$ oxygenates divided by % CF $C_{5-6}$ oxygenates). In certain embodiments, the % CF ratio of $C_{2-4}$ oxygenates to $C_{5-6}$ oxygenates as a percentage of the aqueous carbon feedstock is greater than or equal to 1.0. In certain embodiments, the ratio of $C_{2-4}$ oxygenates to $C_{5-6}$ oxygenates is greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 3.0, greater than or equal to 4.0, greater than or equal to 5.0, greater than or equal to 6.0, greater than or equal to 7.0, greater than or equal to 8.0, greater than or equal to 9.0, greater than or equal to 10.0, greater than or equal to 11.0, greater than or equal to 12.0, greater than or equal to 13.0, greater than or equal to 14.0, greater than or equal to 15.0, greater than or equal to 20.0, greater than or equal to 25.0, greater than or equal to 35.0, greater than or equal to 45.0, or any ratio in between any interval thereof. When the mixture of oxygenates are produced from biomass-derived oxygenated hydrocarbons having a greater than or 50% CF $C_{5-6}$ oxygenated hydrocarbons, having a % CF ratio of $C_{2-4}$ oxygenates to $C_{5-6}$ oxygenates greater than or equal to 1.0 indicates that some of the carbon-carbon bonds are broken. This in turn increases the $H:C_{eff}$ ratio by producing more desirable molecules for the mixture of oxygenates. Without being bound to any particular theory, it is believed that the shorter $C_{2-4}$ oxygenates are better able to react to form the desired aromatic molecules and, thereby, produce fewer undesirable alkanes.

A fourth possible attribute of the mixture of oxygenates is that there is little to no alkanes present. In certain embodiments, the mixture of oxygenates may include alkanes, with the mixture of oxygenates including less than or equal to 10% CF alkanes, where the % CF is calculated by dividing the mass of carbon of the component (e.g. mass of carbon in the alkanes) by the mass of carbon in the mixture of oxygenates and multiplying by 100. In certain embodiments, the mixture of oxygenates include less than or equal to 9% CF alkanes, less than or equal to 8% CF alkanes, less than or equal to 7% CF alkanes, less than or equal to 6% CF alkanes, less than or equal to 5% CF alkanes, less than or equal to 4% CF alkanes, less than or equal to 3% CF alkanes, less than or equal to 2% CF alkanes, or less than or equal to 1% CF alkanes. In certain embodiments when the mixture of oxygenates is produced from biomass-derived oxygenated hydrocarbons, the alkanes constitute less than or equal to 10% CF, less than or equal to 9% CF, less than or equal to 8% CF, less than or equal to 7% CF, less than or equal to 6% CF, less than or equal to 5% CF, less than or equal to 4% CF, less than or equal to 3% CF, less than or equal to 2% CF, or less than or equal to 1% CF, where the % CF is calculated by dividing the mass of carbon of the component (e.g. mass of carbon in the alkanes) by the mass of carbon in the biomass derived aqueous feedstock carbon and multiplying by 100.

The mixture of oxygenates may be produced by any known method. In one embodiment, the mixture of oxygenates is produced using catalytic reforming technologies, such as the bioreforming technology developed by Virent, Inc. (Madison, Wis.), and described in U.S. Pat. No. 7,767,867 (Cortright), U.S. Pat. No. 7,898,664 (Cortright), U.S. Pat. No. 8,053,615 (Cortright et al.), U.S. Pat. No. 8,017,818 (Cortright et al.), and U.S. Pat. No. 7,977,517 (Cortright et al.), all of which are incorporated herein by reference. Alternative methods include fermentation technologies using enzymes or microorganisms, gasification, pyrolysis, hydrothermal liquefaction, solvolysis, and catalytic deconstruction. The mixture of oxygenates may also be derived from natural gas, syn gas or other renewable or non-renewable sources, using Fischer-Tropsch type reactions or reactions directed to the production of alcohols and other mixed oxygenates. Other known methods for producing the mixture of oxygenates may be known to those of skill in the art. The mixture of oxygenates may also be produced by the combining of oxygenates derived from multiple processes and/or sources.

The term "bioreforming" refers to, without limitation, processes for catalytically converting biomass and other carbohydrates to lower molecular weight hydrocarbons and oxygenated compounds, such as alcohols, ketones, cyclic ethers, esters, carboxylic acids, aldehydes, dioxygenates, and other polyoxygenated hydrocarbons, using aqueous phase reforming, hydrogenation, hydrogenolysis, hydrodeoxygenation and/or other conversion processes involving the use of heterogeneous catalysts. Bioreforming also includes the further catalytic conversion of such lower molecular weight oxygenated compounds to $C_{4+}$ compounds.

Figure 2:
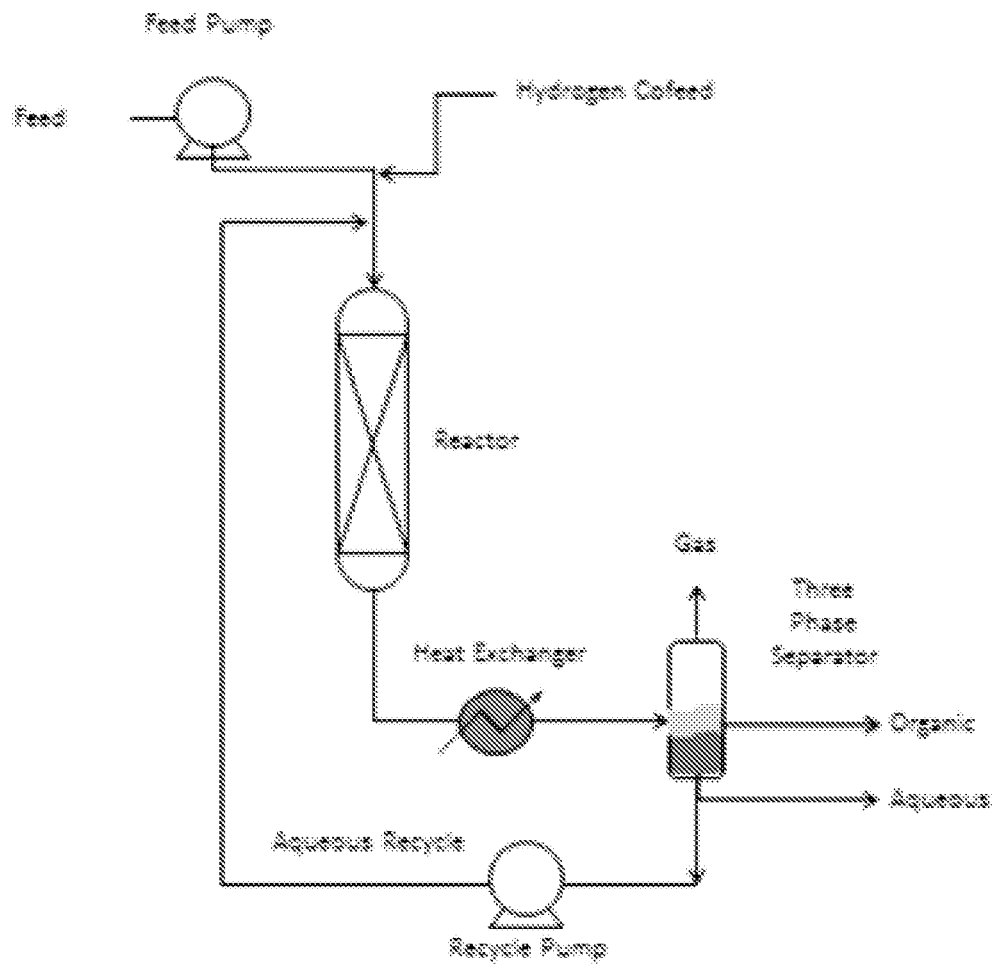
FIG. 2 is an exemplary flow diagram for converting oxygenated hydrocarbons to oxygenated compounds including an optional recycle stream.
Figure 3:
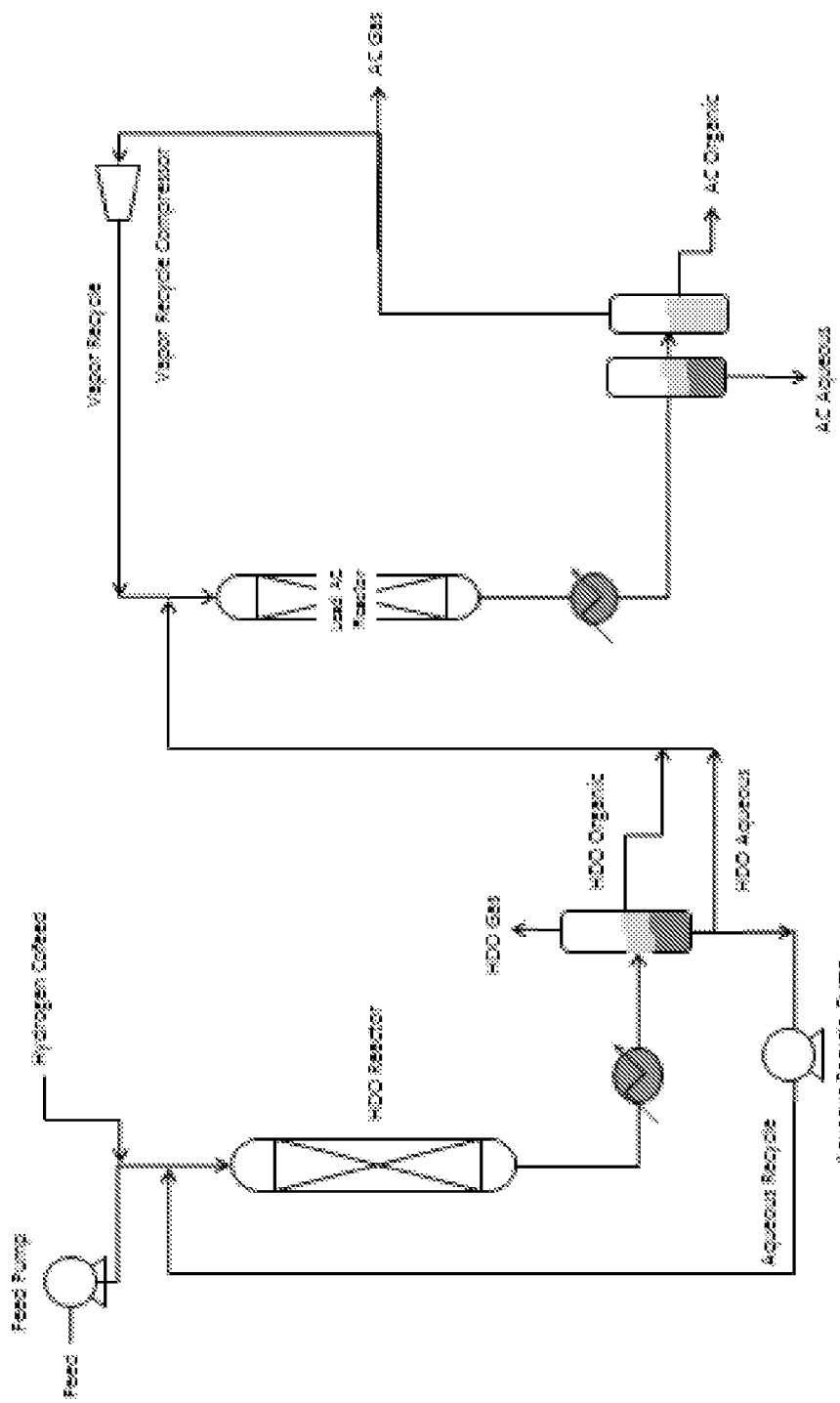
FIG. 3 is an exemplary process flow diagram for converting oxygenated hydrocarbons to liquid fuels and chemicals, including a deoxygenation reactor, an aqueous recycle stream, a condensation reactor, and a vapor phase recycle stream.

FIG. 1 and FIG. 2 provide examples of bioreforming systems capable of producing a mixture of oxygenates in accordance with the present invention. FIG. 1, FIG. 3, FIG. 4, FIG. 5 provide examples of bioreforming systems capable of producing a mixture of hydrocarbons in accordance with the present invention. In these illustrated embodiments, an aqueous feedstock is reacted with hydrogen in the presence of a deoxygenation catalyst to produce a mixture of oxygenates having a $H:C_{eff}$ ratio greater than or equal to 0.5 and less than or equal to 1.7, and one or more of the above described attributes, and the mixture of oxygenates can be reacted in the presence of a condensation catalyst to produce the mixture of hydrocarbons.

DEOXYGENATION CATALYST

Figure 7:
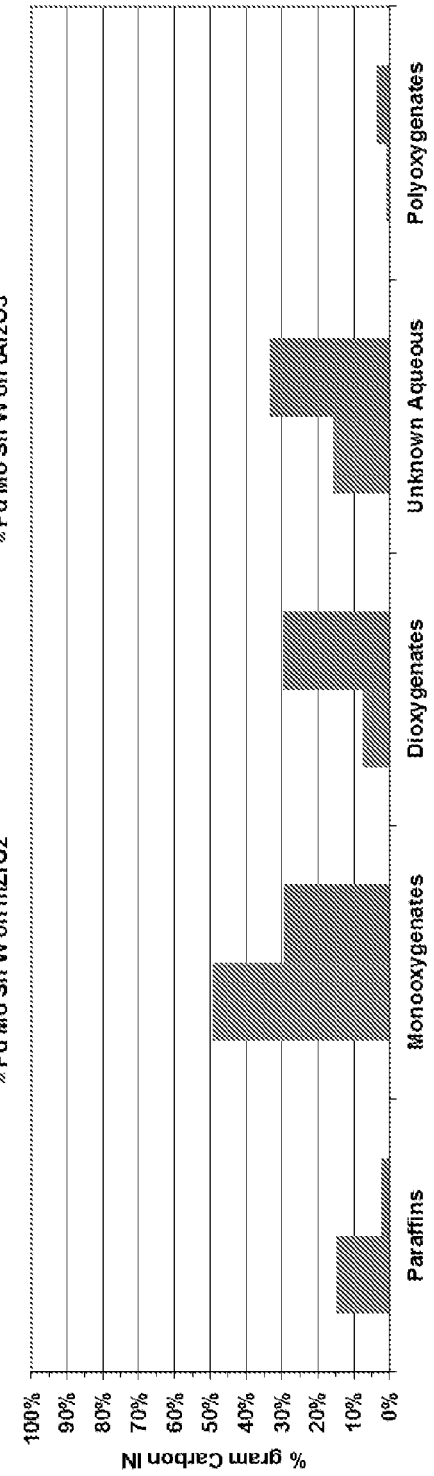
FIG. 7 is an exemplary product distribution illustrating the effect of the deoxygenation catalyst support on the product profile. The catalyst compositions were 2% Pd 2% Mo 0.5% Sn 13.5% W on mZrO2 (reduced to 300° C.) and 2% Pd 2% Mo 0.5% Sn 13.5% W on theta-alumina (reduced to 300° C.).

The deoxygenation catalyst is generally a heterogeneous catalyst capable of catalyzing a reaction between hydrogen and oxygenated hydrocarbons to produce the desired mixture of oxygenates. In general, the deoxygenation catalyst will include a crystalline alumina support and a Group VIII metal, such as Fe, Co, Ni, Ru, Rh, Pd, Os, Ir, or Pt. In contrast to a Group VIII metal acting alone, the crystalline alumina support is able to change the activity of the Group VIII metal to advantageously produce a mixture of oxygenates having the desired $H:C_{eff}$ ratio between 0.5 and 1.7 and, in most instances, the one or more attributes described above. As shown in Example 33 and FIG. 7, the preparation of the deoxygenation catalyst on a theta-alumina support produces substantially more dioxygenates and polyoxygenates than the same catalyst on a zirconia support. The use of the crystalline alumina support also substantially depresses the production of monooxygenates relative to the zirconia support. Finally, the crystalline alumina support substantially depresses the production of alkanes to under 10% of the aqueous feedstock carbon.

The deoxygenation catalyst may include the above elements alone or in combination with a second metal from Group IB, Group IIB, Group IIIB, Group IVB, Group VB, Group VIB, Group VIIB, Group VIII, Group IIIA, Group IVA, and Group VA, including alloys and combinations thereof. The deoxygenation catalyst may also include additional metals from Group IB, Group IIB, Group IIIB, Group IVB, Group VB, Group VIB, Group VIIB, Group VIII, Group IIIA, Group IVA, and Group VA, including alloys and combinations thereof, depending on the particular feedstock and desired mixture of oxygenates. For example, the deoxygenation catalyst may include Ni or Pd, with a second metal of Sn or Mo, or Ni or Pd, with a second metal of Sn and a third metal of Mo. In one embodiment, the deoxygenation catalyst is a heterogeneous catalyst of Pd or Ni and a crystalline alumina support. In another embodiment, the deoxygenation catalyst is a heterogeneous catalyst of Ni and Sn and a crystalline alumina support, or a $Ni_nSn_m$ alloy and a crystalline alumina support, such as $Ni_3Sn_1$ or $Ni_3Sn_2$. In yet another embodiment, the deoxygenation catalyst is a heterogeneous catalyst of Pd, Mo and Sn and a crystalline alumina support, including alloys thereof.

Loading of the first Group VIII metal is in the range of 0.25 wt % to 25 wt %, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second metal is in the range of 0.25-to-1 to 10-to-1, including any ratios between, such as 0.50, 1.00, 2.50, 5.00, and 7.50-to-1. The combination of the catalyst and the support is from 0.25 wt % to 10 wt % of the Group VIII metal.

In one embodiment, the catalyst support is a transitional alumina support, such as a theta-alumina support. The crystalline alumina may be produced via precipitation from aluminum salts, through sol-gel processing, or any other method. The support may be manufactured through peptization of a suitable aluminum hydroxide, preferentially boehmite or pseudoboehmite, with nitric acid in the presence of an organic binder, such as hydroxyethyl cellulose. After forming, the support is then calcined at a final temperature between 900° C. to 1200° C., or greater than or equal to 1000° C. A modifying agent may be added to improve the textural or catalytic properties of the alumina. Such modifying agents include, without limitation, sulfate, silica, Cr, Nb, Mg, Zr, B, Fe, Ce, La, Cu, Co, Mo, Sn, or W.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungsten, silanes, lanthanides, alkali compounds or alkali earth compounds.

Conventional methods for preparing catalyst systems are well known in the art. Common methods include incipient wetting, evaporative impregnation, chemical vapor deposition, wash-coating, magnetron sputtering techniques, and the like. The method chosen to fabricate the deoxygenation catalyst is not critical to the process, with the proviso that different catalysts and methods of preparation will yield different results, depending upon considerations such as overall surface area, porosity, etc. In one embodiment, the catalyst is prepared by combining the Group VIII metal with the second metal from Group IB, Group IIB, Group IIIB, Group IVB, Group VB, Group VIB, Group VIIB, Group VIII, Group IIIA, Group IVA, and Group VA to produce a mixed metal oxide. The mixed metal oxide is then deposited on the crystalline alumina support. In another embodiment the catalyst is prepared by combining a metal from Group IB, Group IIB, Group IIIB, Group IVB, Group VB, Group VIB, Group VIIB, Group VIII, Group IIIA, Group IVA, or Group VA mixed with pseudoboehmite (aluminum hydroxide) then calcined to make a mixed oxide carrier, then a Group VIII metal is deposited on the support. In another embodiment, the crystalline alumina support is calcined to generate a lower surface area. In certain embodiments, calcination of the alumina support may be carried out at temperatures greater than or equal to 800° C., or between 800° C. and 1200° C. In one embodiment the Group VIII metal is Ni and the second metal is selected from Group IVA on a mixed alumina oxide support or the Group VIII metal. In one embodiment the Group VIII metal is Pd and the second metal is selected from either Group VIB or Group IVA or both Group VIB and Group IVA.

In one embodiment, the catalyst is reduced utilizing hydrogen gas at a gas hourly space velocity (GHSV) between 50 and 5000 mL hydrogen gas/mL catalyst/hr and at a pressure between atmospheric and 2000 psig. The catalyst is reduced using a temperature ramp between 0.1° C./min and 10° C./min to a temperature between 20° C. and 600° C. Once the desired temperature is reached, this is followed by a hydrogen soak of between 1 and 24 hours. Following reduction, the catalyst is brought to the desired operating temperatures while in an inert or reducing environment. In certain embodiments, the catalyst is reduced with hydrogen at a GHSV of 500-1000 $hr^{-1}$, 1.0° C./min-8.5° C./min hour temperature gradient at temperatures between 250° C. and 500° C., followed by a 1-4 hour hydrogen soak.

In an alternative embodiment, the catalyst may be pre-sulfided. In another alternative embodiment, the catalyst is sulfided in-situ.

FEEDSTOCKS

Feedstocks comprising oxygenated hydrocarbons useful in the present invention may originate from any source, but are preferably derived from biomass. The feedstocks may be pure materials, purified mixtures, or raw materials such as sugars and starches derived from the processing of corn, sugarcane, beet sugars, rice, wheat, algae, or energy crops. The feedstocks can also be intermediates formed as part of a larger process or in the same process, such as sugar alcohols produced in the initial stage of sugar hydrogenation or sugar degradation products produced from the deconstruction of biomass.

As used herein the terms "lignocellulosic biomass" and "biomass" refer to, without limitation, organic materials produced by plants (e.g., wood, leaves, roots, seeds, stalks, etc.), and microbial and animal metabolic wastes. Common biomass sources include: (1) agricultural residues; such as corn stalks, straw, seed hulls, sugarcane leavings, bagasse, nutshells, and manure from cattle, poultry, and hogs; (2) wood materials; such as wood, bark, sawdust, timber slash, and mill scrap; (3) municipal waste; such as waste paper and yard clippings; (4) energy crops; such as poplars, willows, pine, switch grass, miscanthus, sorghum, alfalfa, prairie bluestream, corn, soybean, and the like; (5) residual solids from industrial processes; such as lignin from pulping processes, acid hydrolysis, or enzymatic hydrolysis; and (6) algae-derived biomass; including carbohydrates and lipids from microalgae (e.g., *Botryococcus braunii, Chlorella, Dunaliella tertiolecta, Gracilaria, Pleurochrysis carterae,* and *Sargassum*) and macroalgae (e.g., seaweed). The term also refers to the primary building blocks of the above, namely, lignin, cellulose, hemicellulose, derivatives thereof, and carbohydrates, such as saccharides (mono-, di-, oligo-, and polysaccharides), sugars, and starches, among others.

The term "oxygenated hydrocarbon" refers to a water-soluble hydrocarbon containing three or more carbon atoms and two or more oxygen atoms, such as carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethyl furfural (HMF), levulinic acid, formic acid, and furfural), each of which is represented herein as $C_{3+}O_{2+}$. As used herein, the term "oxygenated compound" or "oxygenate" refers to a molecule having two or more carbon atoms and one or more oxygen atoms (i.e., $C_{2+}O_{1+}$); the term "monooxygenates" refers to a hydrocarbon molecule containing two or more carbon atoms and one oxygen atom (i.e., $C_{2+}O_1$); the term "dioxygenates" refers to a hydrocarbon molecule containing two or more carbon atoms and two oxygen atoms (i.e., $C_{2+}O_2$); and the term "polyoxygenates" refers to a hydrocarbon molecule containing two or more carbon atoms and three or more oxygen atoms (i.e., $C_{2+}O_{3+}$).

In addition to the oxygenated hydrocarbons, the feedstock may also include lignin, one or more extractives, one or more ash components, or one or more organic species (e.g., lignin derivatives). Extractives include terpenoids, stilbenes, flavonoids, phenolics, aliphatics, lignans, alkanes, proteinaceous materials, amino acids, and other inorganic products. Ash components include Al, Ba, Ca, Fe, K, Mg, Mn, P, S, Si, Zn, etc. Other organic species include 4-ethyl phenol, 4-ethyl-2-methoxy phenol, 2-methoxy-4-propyl phenol, vanillin, 4-propyl syringol, vitamin E, steroids, long chain hydrocarbons, long chain fatty acids, stilbenoids, etc.

In general, the feedstock includes any oxygenated hydrocarbon having three or more carbon atoms and an oxygen-to-carbon ratio of between 0.5:1 to 1:1.2. In one embodiment, the oxygenated hydrocarbon has 3 to 12 carbon atoms or 3 to 6 carbon atoms. In another embodiment, the oxygenated hydrocarbon has more than 12 carbon atoms. Preferred oxygenated hydrocarbons for the present invention are oxygenated hydrocarbons having 5 or 6 continuous carbon atoms, including oxygenated hydrocarbons having more than 5 or 6 total carbon atoms. Non-limiting examples of oxygenated hydrocarbons include monosaccharides, disaccharides, trisaccharides, polysaccharides, oligosaccharides, sugars, sugar alcohols, sugar degradation products, alditols, hemicellulose derivatives, cellulosic derivatives, lignocellulosic derivatives, lignin derivatives, starches, organic acids, polyols, and the like. In one embodiment, the oxygenated hydrocarbon includes polysaccharides, oligosaccharides, trisaccharides, disaccharides, monosaccharides, sugar, sugar alcohols, sugar degradation products, and other polyhydric alcohols. In another embodiment, the oxygenated hydrocarbon is a trisaccharide, a disaccharide, a sugar, such as glucose, fructose, sucrose, maltose, lactose, mannose or xylose, or a sugar alcohol, such as arabitol, erythritol, glycerol, isomalt, lactitol, maltitol, mannitol, sorbitol, xylitol, arabitol, or a glycol. The oxygenated hydrocarbons may also include alcohols derived by the hydrogenation of the foregoing.

In one embodiment, the feedstock may include oxygenated hydrocarbons solvated by a solvent. Non-limiting examples of solvents include: organic solvents, such as ionic liquids, acetone, ethanol, 4-methyl-2-pentanone, and other oxygenated hydrocarbons; dilute acids, such as acetic acid, oxalic acid, hydrofluoric acid; bioreforming solvents; and water. The solvents may be from external sources, recycled, or generated in-situ, such as in-situ generated oxygenated compounds (e.g. $C_{2+}O_{2+}$ oxygenated hydrocarbons).

PRODUCTION OF OXYGENATED COMPOUNDS

The methods, processes, and techniques of bioreforming have been well described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); U.S. Pat. Nos. 7,767,867; 7,989,664; 8,198,486; 8,492,595, and U.S. Patent Application Pub. No. 2013/0289302 (all to Cortright, and entitled "Methods and Systems for Generating Polyols"); U.S. Pat. Nos. 8,053,615; 8,017,818; 7,977,517; 8,362,307; 8,367,882; 8,455,705 and U.S. Patent Application Pub. Nos. 2011/0245542 and 2013/0185992 (all to Cortright and Blommel, and entitled "Synthesis of Liquid Fuels and Chemicals from Oxygenated Hydrocarbons"); U.S. Pat. No. 8,231,857 (to Cortright, and entitled "Catalysts and Methods for Reforming Oxygenated Compounds"); U.S. Pat. No. 8,350,108 (to Cortright et al., and entitled "Synthesis of Liquid Fuels from Biomass"); U.S. Patent Application Ser. No. 2011/0160482 (to Nagaki et al., and entitled "Improved Catalysts for Hydrodeoxygenation of Polyols"); U.S. Patent Application Ser. No. 2011/0009614 (to Blommel et al., and entitled "Processes and Reactor Systems for Converting Sugars to Sugar Alcohols"); International Patent Application No. PCT/US2008/056330 (to Cortright and Blommel, and entitled "Synthesis of Liquid Fuels and Chemicals from Oxygenated Hydrocarbons"); commonly owned U.S. Pat. No. 8,231,857 (to Cortright et al., and entitled "Catalyst and Methods for Reforming Oxygenated Compounds"); and U.S. patent application Ser. No. 13/586,499 (to Blank et al., and entitled "Improved Catalysts for Hydrodeoxygenation of Oxygenated Hydrocarbons"), all of which are incorporated herein by reference. The present invention provides an improvement to the current bioreforming technology in that the catalysts described above are able to produce a mixture of oxygenates for making biomass-derived chemicals and fuels with a high yield of aromatic molecules and a low yield of alkanes.

To produce the mixture of oxygenates, the oxygenated hydrocarbon is combined with water to provide an aqueous feedstock solution having a concentration effective for causing the formation of the desired reaction products. The water-to-carbon ratio on a molar basis is preferably from 0.5:1 to 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least 1.0 weight percent (wt %) of the total solution as an oxygenated hydrocarbon. For instance, the solution may include one or more oxygenated hydrocarbons, with the total concentration of the oxygenated hydrocarbons in the solution being at least 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included.

In one embodiment, the feedstock solution is reacted with hydrogen in the presence of the deoxygenation catalyst at temperatures, pressures, and weight hourly space velocities effective to produce the desired mixture of oxygenates. The specific mixture of oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the deoxygenation catalyst over time, will limit the extent of the reactions that may occur, thereby causing increased yield for higher level dioxygenates and polyoxygenates, with a reduction in ketone, alcohol, and cyclic ether yields.

The reaction temperature and pressures are preferably selected to maintain at least a portion of the feedstock in the liquid phase at the reactor inlet. It is recognized, however, that temperature and pressure conditions may also be selected to more favorably produce the desired products in the vapor-phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In general, the reaction may include a temperature gradient to allow partial deoxygenation of the oxygenated hydrocarbon feedstock at temperatures below the caramelization point of the feedstock. Including a temperature gradient helps prevent the oxygenated hydrocarbons in the feedstock from condensing (e.g., caramelizing) on the catalyst and creating a substantial pressure drop across the reactor that can lead to inoperability of the reactor. The caramelization point, and therefore the required temperature gradient, will vary depending on the feedstock. In one embodiment, the temperature gradient is below about 300° C., or above about 80° C., or between about 150° C. to 300° C., or between about 200° C. to 290° C. In another embodiment, a temperature gradient is not employed.

In condensed phase liquid reactions, the pressure within the reactor must be sufficient to maintain the reactants in the condensed liquid phase at the reactor inlet. For liquid phase reactions, the reaction temperature may be greater than about 80° C., or 110° C., or 120° C., or 130° C., or 140° C. or 150° C., or 160° C., or 170° C., or 180° C., or 190° C., or 200° C., and less than about 350° C., or 325° C., or 290° C., or 280° C., or 270° C., or 260° C., or 250° C., or 240° C., or 230° C., or 220° C. The reaction pressure may be greater than about 70 psig, or 85 psig, or 100 psig, or 115 psig, or 130 psig, or 145 psig, or 160 psig, or 175 psig, or 190 psig, or 205 psig, or 220 psig, or 235 psig, or 250 psig, or 265 psig, or 280 psig, or 295 psig, or 310 psig, or 325 psig, or 375 psig, or 425 psig, or 475 psig, or 550 psig, or 625 psig, or 775 psig, or 925 psig, or 1050 psig, and less than about 3000 psig, or 2950 psig, 2900 psig, 2850 psig, 2800 psig, 2750 psig, 2700 psig, 2650 psig, 2600 psig, 2550 psig, or 2500 psig, or 2450 psig, or 2400 psig, or 2350 psig, or 2300 psig, or 2250 psig, or 2200 psig, or 2150 psig, or 2100 psig, or 2050 psig, or 2000 psig, or 1950 psig, or 1900 psig, or 1850 psig, or 1800 psig. In certain embodiments, the reaction temperature is between about 120° C. and 300° C., or between about 200° C. and 300° C., or between about 270° C. and 290° C., and the reaction pressure is between about 145 and 1950 psig, or between about 1000 and 1900 psig, or between about 1050 and 1800 psig.

For vapor phase reactions, the reaction may be carried out at a temperature where the vapor pressure of the oxygenated hydrocarbon is at least about 0.1 atm, preferably higher (e.g., 350 psig), and the thermodynamics of the reaction are favorable. This temperature will vary depending upon the specific oxygenated hydrocarbon compound used and operating pressure, but is generally greater than about 100° C., or 120° C., or 160° C., or 200° C., or 250° C., and less than about 600° C., or 500° C., or 400° C. for vapor phase reactions. In certain embodiments, the reaction temperature is between about 120° C. and about 500° C., or between about 250° C. and about 400° C.

In general, the reaction should be conducted under conditions where the residence time of the feedstock solution over the catalyst is appropriate to generate the desired products. For example, the WHSV for the reaction may be at least about 0.01 gram of oxygenated hydrocarbon per gram of catalyst per hour, and more preferably the WHSV is about 0.01 to 40.0 g/g hr, including a WHSV of about 0.01, 0.025, 0.05, 0.075, 0.1, 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.77, 0.78, 0.79, 2.61, 2.62, 2.63, etc.).

The hydrogen used in the reaction is preferably external hydrogen, but may be generated in-situ using aqueous phase reforming (in-situ-generated $H_2$ or APR $H_2$), or a combination of APR $H_2$, external $H_2$ or recycled $H_2$, or just simply external $H_2$ or recycled $H_2$. The term "external $H_2$" refers to hydrogen that does not originate from the feedstock solution, but is added to the reactor system from an external source. The term "recycled $H_2$" refers to unconsumed hydrogen, which is collected and then recycled back into the reactor system for further use. External $H_2$ and recycled $H_2$ may also be referred to collectively or individually as "supplemental $H_2$." In general, supplemental $H_2$ may be added for purposes of supplementing the APR hydrogen, or to increase the reaction pressure within the system, or to increase the molar ratio of hydrogen to carbon and/or oxygen in order to enhance the production yield of certain reaction product types.

The amount (moles) of external hydrogen or recycled hydrogen introduced to the feedstock may be between about 0-2400%, 5-2400%, 10-2400%, 15-2400%, 20-2400%, 25-2400%, 30-2400%, 35-2400%, 40-2400%, 45-2400%, 50-2400%, 55-2400%, 60-2400%, 65-2400%, 70-2400%, 75-2400%, 80-2400%, 85-2400%, 90-2400%, 95-2400%, 98-2400%, 100-2400%, 200-2400%, 300-2400%, 400-2400%, 500-2400%, 600-2400%, 700-2400%, 800-2400%, 900-2400%, 1000-2400%, 1100-2400%, or 1150-2400%, or 1200-2400%, or 1300-2400%, or 1400-2400%, or 1500-2400%, or 1600-2400%, or 1700-2400%, or 1800-2400%, or 1900-2400%, or 2000-2400%, or 2100-2400%, or 2200-2400%, or 2300-2400% of the total number of moles of the oxygenated hydrocarbon(s) in the feedstock, including all intervals between. When the feedstock solution, or any portion thereof, is reacted with in-situ generated hydrogen and external hydrogen or recycled hydrogen, the molar ratio of in-situ generated hydrogen to external hydrogen (or recycled hydrogen) is at least 1:100, 1:50, 1:20; 1:15, 1:10, 1:5; 1:3, 1:2, 1:1, 2:1, 3:1, 5:1, 10:1, 15:1, 20:1, 50:1, 100:1 and ratios between (including 4:1, 6:1, 7:1, 8:1, 9:1, 11:1, 12:1, 13:1, 14:1, 15:1, 16:1, 17:1, 18:1 and 19:1, and vice-versa).

OXYGENATE RECYCLE

Recycle streams may be used to maximize product yields and reduce catalyst deactivation. The product of the deoxygenation reaction includes the desired $C_{2+}O_{2+}$ oxygenated compounds and partially deoxygenated hydrocarbons (e.g., disaccharides, monosaccharides, sugars, sugar alcohols, alditols, heavy organic acids, and heavy diols, triols, and other polyols). Recycling these partially deoxygenated hydrocarbons back into the deoxygenation reactor system reduces the carbohydrate concentration entering the deoxygenation reactor system by diluting the carbohydrate-rich feedstock solution with partially deoxygenated hydrocarbons. Diluting the highly reactive carbohydrate feed stream minimizes condensation reactions in the deoxygenation reactor system to help avoid the feedstock condensing on the deoxygenation catalyst, fouling the catalyst, and requiring frequent catalyst changes and/or regeneration. The use of a recycle stream also allows for higher feed stream temperatures. In certain embodiments the preferred recycle to fresh feed weight ratio is in the range of about 0.25-to-1 to 10-to-1, including any ratios between, such as about 0.50, 1.00, 2.50, 4.00, 5.00, and 7.50-to-1.

REACTOR SYSTEM

The deoxygenation reactions may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. In one embodiment, the process is carried out using a continuous-flow system at steady-state equilibrium.

FIG. 1 (without an aqueous recycle stream) and FIG. 2 (with an aqueous recycle stream) are schematic illustrations showing embodiments for converting a biomass-derived oxygenated hydrocarbon feedstock solution to a final desired product using a single reactor containing a deoxygenation catalyst on a support. In one embodiment, multiple deoxygenation reactors are used to control the reaction exotherm. In certain embodiments the feedstock solution includes a solvent (e.g., water, recycled partially deoxygenated hydrocarbons, etc.) combined with one or more oxygenated hydrocarbons, such as carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethyl furfural (HMF), levulinic acid, formic acid, and furfural). As described above, in certain embodiments the feedstock may also include ash components, extractives, phenolics, etc. In one embodiment the feedstock is fed via a pump to the deoxygenation reactor system having the deoxygenation catalyst on a support, where it subsequently reacts with hydrogen to generate an oxygenate mixture having a H:$C_{\mathit{eff}}$ ratio greater than or equal to 0.5 and less than or equal to 1.7, and one or more of the above described attributes.

In one embodiment the mixture is passed through a three-phase separator to separate the non-condensed gases (such as hydrogen, carbon dioxide, methane, ethane, and propane) from an organic products stream and an aqueous stream. The non-condensed gases are removed via an off-gas stream. The non-condensable stream can be either combusted to create process heat (i.e., heat for driving the reaction in the deoxygenation reactor), or sent to a separation system where hydrogen can be recovered for recycle back to the hydrogen stream. The aqueous stream, containing partially deoxygenated hydrocarbons, may be recycled back to the reactor inlet. An aqueous stream purge, including some monooxygenates (e.g., alcohols), can be used to prevent a build-up of water in the reactor system.

CONDENSATION

The mixture of oxygenates produced by the methods described above can be collected and used in industrial applications, or converted into $C_{4+}$ compounds by condensation reactions catalyzed by a condensation catalyst. In particular, the $C_{4+}$ compounds include aryls comprising greater than or equal to 50% CF of the aqueous feedstock carbon and $C_{4+}$ alkanes comprising less than or equal to 20% CF of the aqueous feedstock carbon.

Without being limited to any specific theories, it is believed that the condensation reactions generally consist of a series of steps involving: (a) the dehydration of oxygenates to alkenes; (b) oligomerization of the alkenes; (c) cracking reactions; (d) cyclization of larger alkenes to form aromatics; (e) alkane isomerization; (f) hydrogen-transfer reactions to form alkanes. The reactions may also consist of a series of steps involving (1) aldol condensation to form a β-hydroxyketone or β-hydroxyaldehyde; (2) dehydration of the β-hydroxyketone or β-hydroxyaldehyde to form a conjugated enone; (3) hydrogenation of the conjugated enone to form a ketone or aldehyde, which may participate in further condensation reactions or conversion to an alcohol or hydrocarbon; and (4) hydrogenation of carbonyls to alcohols, or vice-versa. Other condensation reactions may occur in parallel, including aldol condensation, prins reactions, ketonization of acids, and Diels-Alder condensation.

The condensation catalyst will generally be a catalyst capable of forming longer chain compounds by linking two oxygen containing species, or other functionalized compounds (e.g., olefins), through a new carbon-carbon bond, and converting the resulting compound to a hydrocarbon, alcohol or ketone. The condensation catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may include the above alone or in combination with a modifier, such as Ce, La, Y, Sc, P, B, Bi, Li, Na, K, Rb, Cs, Mg, Ca, Sr, Ba, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

In certain embodiments the condensation catalyst may include, without limitation, carbides, nitrides, zirconia, alumina, silica, aluminosilicates, phosphates, zeolites (e.g., ZSM-5, ZSM-11, ZSM-12, ZSM-22, ZSM-23, ZSM-35 and ZSM-48), titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

The condensation catalyst may be self-supporting (i.e., the catalyst does not need another material to serve as a support), or may require a separate support suitable for suspending the catalyst in the reactant stream. In certain embodiments the support is selected from the group consisting of alumina, silica, and zirconia. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 350° C. Other catalyst supports may include those described in further detail below.

In one embodiment the condensation reaction may be performed using a catalyst having acidic functionality. The acid catalysts may include, without limitation, aluminosilicates (zeolites), silica-alumina phosphates (SAPO), aluminum phosphates (AlPO), amorphous silica alumina, zirconia, sulfated zirconia, tungstated zirconia, tungsten carbide, molybdenum carbide, titania, acidic alumina, phosphated alumina, phosphated silica, sulfated carbons, phosphated carbons, acidic resins, heteropolyacids, inorganic acids, and combinations thereof. In one embodiment, the catalyst may also include a modifier, such as Ce, La, Y, Li, Na, K, Rb, Cs, Mg, Ca, Sr, Ba, P, B, Bi, and combinations thereof. The catalyst may also be modified by the addition of a metal, such as Cu, Ag, Au, Pt, Ni, Fe, Co, Ru, Rh, Zn, Ga, In, Pd, Ir, Re, Mn, Cr, Mo, W, Sn, Os, alloys and combinations thereof, to provide metal functionality, and/or sulfides and oxides of Ti, Zr, V, Nb, Ta, Mo, Cr, W, Mn, Re, Al, Ga, In, Fe, Co, Ir, Ni, Si, Cu, Zn, Sn, P, and combinations thereof. Tungstated zirconia, an exemplary catalyst for use in the present process, may be modified with Cu, Pd, Ag, Pt, Ru, Re, Ni, Sn and combinations thereof. The acid catalyst may be homogenous, self-supporting or adhered to any one of the supports further described below, including supports containing carbon, silica, alumina, zirconia, titania, vanadia, ceria, heteropolyacids, alloys and mixtures thereof.

The condensation catalyst may be a zeolite catalyst. The term "zeolite" as used herein refers not only to microporous crystalline aluminosilicate, but also microporous crystalline metal-containing aluminosilicate structures, such as galloaluminosilicates and gallosilicates. In such instances, In, Zn, Fe, Mo, Ag, Au, Ni, P, Y, Ta, and lanthanides may be exchanged onto zeolites to provide the desired activity. Metal functionality may be provided by metals such as Cu, Ag, Au, Pt, Ni, Fe, Co, Ru, Zn, In, Rh, Pd, Ir, Re, Mn, Cr, Mo, W, Sn, Os, alloys and combinations thereof.

The condensation catalyst may include one or more zeolite structures comprising cage-like structures of silica-alumina. Zeolites are crystalline microporous materials with well-defined pore structures. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates, optionally modified with cations, such as Ga, In, Zn, Mo, and mixtures of such cations, as described, for example, in U.S. Pat. No. 3,702, 886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. No. 3,702,886; Re. 29,948 (highly siliceous ZSM-5); U.S. Pat. Nos. 4,100,262 and 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat. No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference. An exemplary condensation catalyst is a ZSM-5 zeolite modified with Cu, Pd, Ag, Pt, Ru, Re, Ni, Sn, or combinations thereof.

As described in U.S. Pat. No. 7,022,888, the condensation catalyst may be a bifunctional pentasil zeolite catalyst including at least one metallic element from the group of Cu, Ag, Au, Pt, Ni, Fe, Co, Ru, Zn, Cd, In, Rh, Pd, Ir, Re, Mn, Cr, Mo, W, Sn, Os, alloys and combinations thereof, or a modifier from the group of In, Zn, Fe, Mo, Au, Ag, Y, Sc, Ni, P, Ta, lanthanides, and combinations thereof. The zeolite may have strong acidic sites, and may be used with reactant streams containing an oxygenated hydrocarbon at a temperature of below 580° C. The bifunctional pentasil zeolite may have ZSM-5, ZSM-8 or ZSM-11 type crystal structure consisting of a large number of 5-membered oxygen-rings (i.e., pentasil rings). In one embodiment the zeolite will have a ZSM-5 type structure.

Alternatively, solid acid catalysts such as alumina modified with phosphates, chloride, silica, and other acidic oxides may be used in the process. Also, sulfated zirconia, phosphated zirconia, titania zirconia, or tungstated zirconia may provide the necessary acidity. Re and Pt/Re catalysts are also useful for promoting condensation of oxygenates to $C_{5+}$ hydrocarbons and/or $C_{5+}$ mono-oxygenates. The Re is sufficiently acidic to promote acid-catalyzed condensation. In certain embodiments, acidity may also be added to activated carbon by the addition of either sulfates or phosphates.

The specific $C_{4+}$ compounds produced will depend on various factors, including, without limitation, the type of oxygenated compounds in the reactant stream, condensation temperature, condensation pressure, the reactivity of the catalyst, and the flow rate of the reactant stream as it affects the space velocity, GHSV, LHSV, and WHSV. In certain embodiments, the reactant stream is contacted with the condensation catalyst at a WHSV that is appropriate to produce the desired hydrocarbon products. In one embodiment the WHSV is at least 0.1 grams of volatile ($C_{2+}O_{1-3}$) oxygenates in the reactant stream per gram catalyst per hour.

In another embodiment the WHSV is between 0.1 to 10.0 g/g hr, including a WHSV of 1, 2, 3, 4, 5, 6, 7, 8, 9, 10 g/g hr, and increments between.

In certain embodiments the condensation reaction is carried out at a temperature and pressure at which the thermodynamics of the proposed reaction are favorable. For volatile $C_{2+}O_{1-3}$ oxygenates the reaction may be carried out at a temperature where the vapor pressure of the volatile oxygenates is at least 0.1 atm (and preferably a good deal higher). The condensation temperature will vary depending upon the specific composition of the oxygenated compounds. The condensation temperature will generally be greater than 80° C., or 100° C., or 125° C., or 150° C., or 175° C., or 200° C., or 225° C., or 250° C., and less than 500° C., or 450° C., or 425° C., or 375° C., or 325° C., or 275° C. For example, the condensation temperature may be between 80° C. to 500° C., or between 125° C. to 450° C., or between 250° C. to 425° C. The condensation pressure will generally be greater than 0 psig, or 10 psig, or 100 psig, or 200 psig, and less than 2000 psig, or 1800 psig or, or 1600 psig, or 1500 psig, or 1400 psig, or 1300 psig, or 1200 psig, or 1100 psig, or 1000 psig, or 900 psig, or 700 psig. For example, the condensation pressure may be greater than 0.1 atm, or between 0 and 1500 psig, or between 0 and 1200 psig.

CONDENSATION PRODUCTS

The condensation reactions of the present invention can be used in the production of $C_{4+}$ alkanes, $C_{4+}$ alkenes, $C_{5+}$ cycloalkanes, $C_{5+}$ cycloalkenes, aryls, fused aryls, polycyclic compounds, $C_{4+}$ alcohols, $C_{4+}$ ketones, $C_{4+}$ furans and mixtures thereof, with an advantageously high proportion of aryls and a low proportion of alkanes. In particular, the use of the above described mixture of oxygenates results in an aryl yield greater than or equal to 50% CF of the aqueous feedstock carbon and a $C_{4+}$ alkane yield less than or equal to 20% CF of the aqueous feedstock carbon. In certain embodiments, the aryls yield can be greater than or equal to 55 wt %, greater than or equal to 60% CF, or greater than or equal to 65% CF of the aqueous feedstock carbon. In certain embodiments, the $C_{4+}$ alkane yield is less than or equal to 15% CF, less than or equal to 10% CF, or less than or equal to 5% CF of the aqueous feedstock carbon. In certain other embodiments, the product may further comprise $C_{1-3}$ alkanes with the total $C_{1+}$ alkane yield less than or equal to 20% CF, less than or equal to 15% CF, less than or equal to 10% CF, or less than or equal to 5% CF of the aqueous feedstock carbon.

In certain embodiments, the aryls yield is greater than or equal to 55% CF of the aqueous feedstock carbon and the $C_{4+}$ alkane yield is less than or equal to 15% CF of the aqueous feedstock carbon. In another embodiment the aryls yield is greater than or equal to 60% CF of the aqueous feedstock carbon and the $C_{4+}$ alkane yield is less than or equal to 10% CF of the aqueous feedstock carbon. In further embodiments, the aryls yield is greater than or equal to 55% CF of the aqueous feedstock carbon and the $C_{1+}$ alkane yield is less than or equal to 15% CF of the aqueous feedstock carbon. In yet other embodiments, the aryls yield is greater than or equal to 60% CF of the aqueous feedstock carbon and the $C_{1+}$ alkane yield is less than or equal to 10% CF of the aqueous feedstock carbon.

The $C_{4+}$ alkanes and $C_{4+}$ alkenes have from 4 to 30 carbon atoms ($C_{4-30}$ alkanes and $C_{4-30}$ alkenes) and may be branched or straight chained alkanes or alkenes. The $C_{4+}$ alkanes and $C_{4+}$ alkenes may also include fractions of $C_{4-9}$, $C_{7-14}$, $C_{12-24}$ alkanes and alkenes, respectively, with the $C_{4-9}$ fraction directed to gasoline, the $C_{7-16}$ fraction directed to jet fuels, and the $C_{11-24}$ fraction directed to diesel fuel and other industrial applications, such as chemicals. Examples of various $C_{4+}$ alkanes and $C_{4+}$ alkenes include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{5+}$ cycloalkanes and $C_{5+}$ cycloalkenes have from 5 to 30 carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-12}$ alkyl, a straight chain $C_{1-12}$ alkyl, a branched $C_{3-12}$ alkylene, a straight chain $C_{1-12}$ alkylene, a straight chain $C_{2-12}$ alkylene, a phenyl or a combination thereof. By way of further example, at least one of the substituted groups include a branched $C_{3-4}$ alkyl, a straight chain $C_{1-4}$ alkyl, a branched $C_{3-4}$ alkylene, straight chain $C_{1-4}$ alkylene, straight chain $C_{2-4}$ alkylene, a phenyl or a combination thereof. Examples of desirable $C_{5+}$ cycloalkanes and $C_{5+}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, propyl-cyclohexane, butyl-cyclopentane, butyl-cyclohexane, pentyl-cyclopentane, pentyl-cyclohexane, hexyl-cyclopentane, hexyl-cyclohexane, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-12}$ alkyl, a straight chain $C_{1-12}$ alkyl, a branched $C_{3-12}$ alkylene, a straight chain $C_{2-12}$ alkylene, a phenyl or a combination thereof. By way of further example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aryls include, without limitation, benzene, toluene, xylene (dimethylbenzene), ethyl benzene, para xylene, meta xylene, ortho xylene, $C_{9+}$ aromatics, butyl benzene, pentyl benzene, hexyl benzene, heptyl benzene, oxtyl benzene, nonyl benzene, decyl benzene, undecyl benzene, and isomers thereof.

Fused aryls will generally consist of bicyclic and polycyclic aromatic hydrocarbons, in either an unsubstituted, mono-substituted, or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, naphthalene, anthracene, and isomers thereof.

Polycyclic compounds will generally consist of bicyclic and polycyclic hydrocarbons, in either an unsubstituted, mono-substituted, or multi-substituted form. Although polycyclic compounds generally include fused aryls, as used herein the polycyclic compounds generally have at least one saturated or partially saturated ring. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, tetrahydronaphthalene and decahydronaphthalene, and isomers thereof.

The $C_{4+}$ alcohols may also be cyclic, branched or straight chained, and have from 4 to 30 carbon atoms. In general, the $C_{4+}$ alcohols may be a compound according to the formula $R^1$—OH, wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and combinations thereof. Examples of desirable $C_{4+}$ alcohols include, without limitation, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The $C_{4+}$ ketones may also be cyclic, branched or straight chained, and have from 4 to 30 carbon atoms. In general, the $C_{4+}$ ketone may be a compound according to the formula

wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and a combination thereof. Examples of desirable $C_{4+}$ ketones include, without limitation, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

LIQUID FUELS AND CHEMICALS

The $C_{4+}$ compounds derived from the condensation reactions described above can be fractionated and used in aromatic-rich liquid fuels, such as gasoline, jet fuel (kerosene) or diesel fuel. The $C_{4+}$ compounds can also be fractionated and used in chemical processes, such as those common to the petro-chemical industry. For example, the product stream from the process can be fractionated to collect xylenes for use in the production of phthalic acid, polyethylene terephthalate (PET), and ultimately renewable plastics or solvents. Benzene can also be collected and processed for the production of renewable polystyrenes, polycarbonates, polyurethane, epoxy resins, phenolic resins, and nylon. Toluene can be collected and processed for the production of toluene diisocyanate, and ultimately renewable solvents, polyurethane foam or TNT, among others.

In one embodiment, the $C_{4+}$ compounds derived from the process are separated into various distillation fractions by any means known for liquid fuel compositions. In such applications, the product stream having at least one $C_{4+}$ compound derived from the process is separated into more than one distillation fraction, wherein at least one of the distillation fractions is a lighter, moderate or heavier fraction. The lighter fractions, primarily $C_{4-9}$, i.e., $C_4$, $C_5$, $C_6$, $C_7$, $C_8$, and $C_9$, may be separated for gasoline use. The moderate fractions, primarily $C_{7-14}$, i.e., $C_7$, $C_8$, $C_9$, $C_{10}$, $C_{11}$, $C_{12}$, $C_{13}$, and $C_{14}$, may be separated for use as kerosene, e.g., for jet fuel use. Heavier fractions, primarily $C_{12-24}$, i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, and $C_{24}$, may be separated for diesel fuel use. The heaviest fractions, $C_{25+}$ and $C_{30+}$, i.e., $C_{25}$, $C_{26}$, $C_{27}$, $C_{28}$, $C_{29}$, $C_{30}$, $C_{31}$, $C_{32}$, $C_{33}$, $C_{34}$, $C_{35}$, etc., may be used as lubricants, fuel oils, or may be cracked to produce additional fractions for use in gasoline, kerosene and/or diesel fractions.

Because the $C_{4+}$ compounds are derived from biomass, the age of the compounds, or fractions containing the compounds, is less than 500 years old, preferably less than 40 years old, more preferably less than 20 years old, as calculated from the $^{14}C$ concentration of the component.

The following examples are to be illustrative and should not be construed to limit the scope of protection sought, which is defined by the appended claims.

EXAMPLES

Example 1

Production of Aromatic Molecules

Feeds composed of a mixture of oxygenates and water as defined in Table 1 were reacted in the presence of a Ni-modified ZSM-5 catalyst to determine the impact of feed composition on product selectivity and yield. The reactor system is shown in FIG. 1. The catalyst was loaded as an 8 inch packed bed in a 1 inch outer diameter Inconel reactor. Before feed was introduced, the catalyst was reduced in-situ. The conditions were set at 350° C., 100 psig, and a weight hourly space velocity (WHSV) of 2 grams of oxygenated hydrocarbons per gram of catalyst per hour.

TABLE 1

Feed composition.

| Feed | Water (wt %) | n-propanol (wt %) [% CF] | Prop. Glycol (wt %) [% CF] | % CF Ratio | $H:C_{eff}$ |
|---|---|---|---|---|---|
| 1 | 48.8 | 51.2 [100] | N/A [0.0] | 0.0 | 2.0 |
| 2 | 51.6 | 23.8 [55.1] | 24.6 [44.9] | 0.8 | 1.7 |
| 3 | 52.7 | 13.0 [32.4] | 34.3 [67.6] | 2.0 | 1.55 |
| 4 | 53.6 | 3.7 [9.9] | 42.7 [90.1] | 9.1 | 1.4 |

Table 2 shows the conversion of the model feeds to hydrocarbon products. Each feed exhibited comparable feed conversion, and at least 98% of the feed carbon was converted to hydrocarbon products. Although the feedstocks exhibited similar total conversion, product selectivity varied significantly. As the content of propylene glycol in the feed increased, an increase in the aromatic hydrocarbons was observed along with a reduction in alkane production. As Table 2 shows that the increase of aromatic hydrocarbon production came at the expense of the alkane production.

TABLE 2

Product composition as a function of feed composition.

| | Product Composition (% CF) | | | | |
|---|---|---|---|---|---|
| Feed | $CO + CO_2$ | Paraffins | Olefins | Aromatics | Oxygenates |
| 1 | 0.1 | 46.9 | 7.8 | 30.6 | 0.6 |
| 2 | 0.3 | 17.2 | 8.7 | 51.1 | 1.3 |
| 3 | 0.6 | 10.4 | 8.3 | 60.4 | 2.0 |
| 4 | 1.1 | 6.7 | 10.1 | 65.4 | 1.5 |

Example 2

Production of Aromatic Molecules

Feeds composed of a mixture of oxygenates and water as defined in Table 3 were reacted in the presence of a Ni-modified ZSM-5 catalyst to determine the impact of feed composition on product selectivity and yield. The reactor system is shown in FIG. 1. The catalyst was loaded as an 8 inch packed bed in a 1 inch outer diameter Inconel reactor. Before feed was introduced, the catalyst was reduced in-situ. The conditions were set at 350° C., 100 psig, and a weight hourly space velocity (WHSV) of 2 grams of oxygenated hydrocarbons per gram of catalyst per hour.

TABLE 3

Feed Composition

| Feed | Water (wt %) | n-propanol (wt %) [% CF] | Propyl Propanoate (wt %) [% CF] | % CF Ratio | $H:C_{eff}$ |
|---|---|---|---|---|---|
| 1 | 48.8 | 51.2 [100] | N/A [0.0] | 0.0 | 2.0 |
| 2 | 44.1 | 30.7 [60.7] | 25.2 [39.3] | 0.8 | 1.7 |
| 3 | 41.3 | 18.6 [37.0] | 40.1 [63.0] | 2.2 | 1.55 |

Table 4 shows the conversion of the model feeds to hydrocarbon products. Each feed exhibited comparable feed conversion, and at least 96% of the feed carbon was converted to hydrocarbon products. Although the feedstocks exhibited similar total conversion, product selectivity varied significantly. As the content of propyl propanoate in the feed increased, an increase in the aromatic hydrocarbons was observed. In contrast, alkane production decreased as the propylene glycol in the feed increased. As the $H:C_{eff}$ decreased, the aromatic hydrocarbon production increased and the alkane production decreased.

TABLE 4

Product composition as a function of feed composition

| | Product Composition (% CF) | | | | |
|---|---|---|---|---|---|
| Feed | CO + CO$_2$ | Paraffins | Olefins | Aromatics | Oxygenates |
| 1 | 0.1 | 46.9 | 7.8 | 30.6 | 0.4 |
| 2 | 0.3 | 21.1 | 13.3 | 49.1 | 1.3 |
| 3 | 0.3 | 8.1 | 16.7 | 51.0 | 3.4 |

Example 3

Production of Aromatic Molecules

Feeds composed of a mixture of oxygenates and water as defined in Table 5 were reacted with a Ni-modified ZSM-5 catalyst to determine the impact of feed composition on product selectivity and yield. The reactor system is shown in FIG. 1. The catalyst was loaded as an 8 inch packed bed in a 1 inch outer diameter Inconel reactor. Before feed was introduced, the catalyst was reduced in-situ. The conditions were set at 350° C., 100 psig, and a weight hourly space velocity (WHSV) of 2 grams of oxygenated hydrocarbons per gram of catalyst per hour.

TABLE 5

Feed Composition

| Feed | Water (wt %) | n-propanol (wt %) [% CF] | Propionic Acid (wt %) [% CF] | % CF Ratio | H:C$_{eff}$ |
|---|---|---|---|---|---|
| 1 | 48.8 | 51.2 [100] | N/A [0.0] | 0.0 | 2.0 |
| 2 | 44.8 | 33.9 [66.8] | 21.3 [33.2] | 0.5 | 1.55 |

Table 6 shows the conversion of the model feeds to hydrocarbon products. Each feed exhibited comparable feed conversion, and at least 97% of the feed carbon was converted to hydrocarbon products. Although the feedstocks exhibited similar total conversion, product selectivity varied significantly. As the content of propionic acid in the feed increased, an increase in the aromatic hydrocarbons was observed. In contrast, alkane production decreased as the propylene glycol in the feed increased. As the H:C$_{eff}$ decreased, the aromatic hydrocarbon production increased and the alkane production decreased.

TABLE 6

Product composition as a function of feed composition

| | Product Composition (% CF) | | | | |
|---|---|---|---|---|---|
| Feed | CO + CO$_2$ | Paraffins | Olefins | Aromatics | Oxygenates |
| 1 | 0.1 | 46.9 | 7.8 | 30.6 | 0.4 |
| 2 | 0.4 | 10.6 | 14.0 | 55.3 | 3.0 |

Example 4

NiSn Catalyst Synthesis

In a beaker, 4.515 g of Tin (IV) Chloride pentahydrate (Riedel de Haen) was diluted to 45 mL with water and added via incipient wetness technique to 75 grams of a crystalline alumina (Norpro). The material was transferred to a static oven and dried for 3 hours at 120° C. After drying, the material was placed in a muffle furnace equipped with an air sweep gas flowing at 30 scfh. The catalyst was calcined by ramping 1.6° C./min to 400° C. and holding for 6 hours. After cooling, a 45 mL solution containing 32.766 g of Nickel (II) Nitrate (Alfa Aesar) was added to the catalyst via incipient wetness. The material was transferred to a static oven and dried for 3 hours at 120° C. After drying, the material was placed in a muffle furnace equipped with an air sweep gas flowing at 30 scfh.

Example 5

Production of Oxygenates

The deoxygenation catalyst from Example 4 was tested at three different temperature profiles outlined in Table 7 to examine the impact of temperature on feed conversion and product selectivity. The reactor system is shown in FIG. 2. The catalyst was loaded as a 10 inch packed bed in a 1 inch outer diameter Inconel reactor. Before feed was introduced, the catalyst was reduced in-situ. The conditions were set at the desired temperature profile outlined in Table 7, 1050 psig, a weight hourly space velocity (WHSV) of 0.40 grams of sugars per gram of catalyst per hour, a hydrogen co-feed of approximately 2 moles H$_2$ per 1 mole carbon feed, and an aqueous recycle ratio of 1 mass flow rate aqueous recycle to 1 mass flow rate feed. The feed was composed of 45 wt % glucose, 15 wt % xylose, and 40 wt % water with approximately 1000 ppm of propionic acid to prevent bacterial growth.

TABLE 7

Temperature profile.

| Temperature Profile | Inlet Temperature (° C.) | Outlet Temperature (° C.) |
|---|---|---|
| 1 | 150 | 230 |
| 2 | 160 | 240 |
| 3 | 165 | 270 |

As is shown in Table 8, nearly all of the sugars were converted at each of the temperature profiles. As the temperature profile was increased, a shift in product selectivity from sugar alcohols to primarily diols and unidentified aqueous compounds was observed. Although a portion of the production composition is unidentified, the unidentified compounds are not monoxygenates and most likely di- and polyoxygenates.

TABLE 8

Product composition as a function of temperature profile.
Product Composition (% CF)

| Temp. Profile | $C_{4-}$ Paraffins | $C_{5+}$ Paraffins | Diols | Acids | Triols | Sugar Alcohols | Sugars | Unknown Aqueous |
|---|---|---|---|---|---|---|---|---|
| 1 | 0.01 | 0.03 | 9.99 | 0.25 | 4.14 | 39.08 | 0.22 | 42.00 |
| 2 | 0.00 | 0.32 | 19.88 | 0.27 | 6.64 | 19.33 | 0.02 | 53.22 |
| 3 | 0.03 | 0.21 | 34.17 | 0.44 | 0.99 | 0.82 | 0.00 | 60.97 |

Example 6

Deoxygenation Catalyst Synthesis

A tetrametallic catalyst containing 1 wt % Pd, 1 wt % Mo, 0.25 wt % Sn, and 5% W on monoclinic zirconia was prepared using incipient wetness techniques. An aqueous solution with a volume equal to the incipient wetness volume for the monoclinic zirconia and containing 12.18 g of ammonium tungsten oxide hydrate (Alfa Aesar) was added to 165 g of monoclinic zirconia (Norpro) via incipient wetness. The catalyst was dried at 130° C. for 2 hours. The catalyst was then calcined in air from ambient temperature to 400° C. at 1.6° C./min. Once the desired temperature was reached, the catalyst was soaked in air for an additional 6 hours. An aqueous solution of 2 molar ammonium nitrate (Sigma Aldrich) with a volume equal to the incipient wetness volume of the catalyst to be impregnated and containing 1.22 g of tin (IV) chloride pentahydrate (Riedel de Haen) was added to the calcined catalyst via incipient wetness. The catalyst was dried at 130° C. for 2 hours. The catalyst was then calcined in air from ambient temperature to 200° C. at 2° C./min. From 200° C. to 220° C. the temperature ramp was slowed to 0.1° C./min. Finally, the temperature ramp rate was increased to 2° C./min from 220° C. to 400° C. Once the desired temperature was reached, the catalyst was soaked in air for an additional 6 hours. An aqueous solution of 2 molar ammonium nitrate (Sigma Aldrich) with a volume equal to the incipient wetness volume for the catalyst to be impregnated and containing 3.064 g of ammonium molybdate tetrahydrate (Sigma Aldrich) was added to the calcined catalyst. The catalyst was dried at 130° C. for 2 hours. An aqueous solution of 2 molar ammonium nitrate (Sigma Aldrich) with a volume equal to the incipient wetness volume for the catalyst to be impregnated and containing 4.193 g of palladium (II) nitrate hydrate (Alfa Aesar) was added to the calcined catalyst. The catalyst was dried at 130° C. for 2 hours. The catalyst was then calcined with air from ambient temperature to 200° C. at 2° C./min. From 200° C. to 220° C. the temperature ramp was slowed to 0.1° C./min. Finally, the temperature ramp rate was increased to 2° C./min from 220° C. to 400° C. Once the desired temperature was reached, the catalyst was soaked in air for an additional 6 hours.

Example 7

Production of Oxygenates

Example 8 compares the oxygenate product composition produced by the two different deoxygenation catalysts from Example 4 and Example 6. The catalysts were operated to produce a mixture of oxygenated hydrocarbons using a reactor system as shown in FIG. 2.

The deoxygenation catalyst from Example 6 was loaded as an 11.5 inch packed bed in a 1 inch outer diameter Inconel reactor. Before feed was introduced, the catalyst was reduced in-situ. The conditions were set at a temperature profile of 170-280° C., 1800 psig, a weight hourly space velocity (WHSV) of 0.40 grams of sugars per gram of catalyst per hour, a hydrogen co-feed of approximately 1.5 moles $H_2$ per 1 mole carbon fed, and an aqueous recycle ratio of 4 mass flow rate aqueous recycle to 1 mass flow rate feed. The feed was composed of 60 wt % sucrose and 40 wt % water with approximately 1000 ppm of propionic acid to prevent bacterial growth.

The deoxygenation catalyst from Example 4 was loaded as a 10 inch packed bed in a 1 inch outer diameter Inconel reactor. Before feed was introduced, the catalyst was reduced in-situ. The conditions were set at a temperature profile of 175-270° C., 1050 psig, a weight hourly space velocity (WHSV) of 0.40 grams of sugars per gram of catalyst per hour, a hydrogen co-feed of approximately 2 moles $H_2$ per 1 mole carbon fed, and an aqueous recycle ratio of 1 mass flow rate aqueous recycle to 1 mass flow rate feed. The feed was composed of 45 wt % glucose, 15 wt % xylose, and 40 wt % water with approximately 1000 ppm of propionic acid to prevent bacterial growth.

Table 9 shows that the product profiles for each deoxygenation catalyst are different. The catalyst from Example 6 results in greater deoxygenation as shown by increased production of paraffin and monooxygenate species. In contrast, the catalyst from Example 4 produces hydrocarbons with more oxygen as highlighted by the production of dioxygenate and unidentified aqueous species. These results demonstrate that the catalyst from Example 4 removes some oxygen from the oxygenated hydrocarbon feed to increase the $H:C_{eff}$ ratio. These results also demonstrate that the catalyst of Example 4 removes less oxygen than the catalyst of Example 6, which results in the catalyst of Example 4 producing a product composition having a lower $H:C_{eff}$ ratio than the catalyst of Example 6.

TABLE 9

Deoxygenation product composition.

| | | Catalyst | |
|---|---|---|---|
| | | Example 6 | Example 4 |
| Product Comp. (% CF) | $CO + CO_2$ | 0.61 | 1.05 |
| | Paraffins | 5.36 | 0.23 |
| | Monooxygenates | 37.46 | 9.16 |
| | Dioxygenates | 23.75 | 35.59 |
| | Un. Aqueous | 27.57 | 49.77 |
| | Polyoxygenates | 2.10 | 1.78 |

Table 10 shows a more detailed breakdown of the product composition. The deoxygenation catalyst from Example 6 produces primarily alcohol and cyclic ether monooxygenates. In contrast, the deoxygenation catalyst of Example 4 produces primarily diols and unidentified aqueous compounds, which are believed to be di- and polyoxygenates.

TABLE 10

Detailed product composition.

| | | Catalyst | |
|---|---|---|---|
| | | Example 6 | Example 4 |
| Product Comp. | $CO + CO_2$ | 0.61 | 1.05 |
| (% CF) | $C_{4-}$ Paraffins | 2.45 | 0.03 |
| | $C_{5+}$ Paraffins | 2.91 | 0.2 |
| | Alcohols | 20.31 | 3.17 |
| | Ketones | 4.37 | 1.73 |
| | Cyclic Ethers | 11.11 | 5.63 |
| | Cyclic Ketones | 1.67 | 0.07 |
| | Hydroxyketones + Diones | 1.83 | 1.44 |
| | Diols | 18.29 | 33.46 |
| | Acids | 3.63 | 0.67 |
| | Unidentified Aqueous | 27.57 | 49.77 |
| | Polyoxygenates | 2.10 | 1.78 |

Table 11 shows the carbon number breakdown of the identified carbon species in the product. The catalyst from Example 6 maintains the carbon backbone of the sugar feed and produces a small amount of longer chain compounds. In contrast, the catalyst of Example 4 produces shorter chain molecules, primarily in the $C_2$-$C_4$ range.

TABLE 11

Carbon number breakdown.

| | | Catalyst | |
|---|---|---|---|
| | | Example 6 | Example 4 |
| Product Comp. | $C_1$ | 0.47 | 0.40 |
| (% CF) | $C_2$ | 3.90 | 5.75 |
| | $C_3$ | 26.49 | 23.76 |
| | $C_4$ | 5.50 | 7.64 |
| | $C_5$ | 2.62 | 4.65 |
| | $C_6$ | 28.60 | 4.67 |
| | $C_7$ | 0.56 | 0.53 |
| | $C_8$ | 1.30 | 0.00 |
| | $C_9$ | 0.71 | 0.00 |
| | $C_{10}$ | 0.32 | 0.00 |
| | $C_{11}$ | 0.12 | 0.00 |
| | $C_{12}$ | 0.09 | 0.00 |

Collectively, Table 9 through Table 11 show that the product compositions are different. The products of the deoxygenation catalyst of Example 4 tend to be oxygenated compounds having 2 to 4 carbon atoms and 2 or 3 oxygen atoms. Molecules of this type often have $H:C_{eff}$ ratios approximately between 0.5 and 1.5. As a result, the product composition of the deoxygenation catalyst of Example 4 has a lower $H:C_{eff}$ than the catalyst of Example 6.

Example 8

Production of Aromatic Molecules

The products from Example 7 were processed downstream across a Ni-modified ZSM-5 condensation catalyst to evaluate the hydrocarbon yield and selectivity, short term catalyst deactivation, and process operability. The deoxygenation catalyst from Example 6 and the deoxygenation catalyst from Example 4 were tested in the reactor systems shown in FIG. 3 and FIG. 4, respectively. The products from the deoxygenation catalyst from Example 6 were processed across a Ni-modified ZSM-5 condensation catalyst loaded as two 13.5 inch packed beds in 1 inch outer diameter Inconel reactors. The conditions were set at 400° C., 100 psig, a weight hourly space velocity (WHSV) of 0.4 grams of sugars per gram of catalyst per hour, and a vapor recycle ratio of 1.9 mass flow rate vapor recycle to 1 mass flow rate feed.

The products from the deoxygenation catalyst from Example 4 were processed across a Ni-modified ZSM-5 condensation catalyst loaded as a 12 inch packed bed in a 1 inch outer diameter Inconel reactor. The conditions were set at 375° C., 100 psig, a weight hourly space velocity (WHSV) of 0.4 grams of sugars per gram of catalyst per hour, and no vapor recycle.

Table 12 shows the impact of the different oxygenate feeds on the hydrocarbon product yield and selectivity. Using the deoxygenation catalyst of Example 4 increased the aromatics yield and decreased the paraffin yield when compared against the deoxygenation catalyst of Example 6. Most notably, the paraffin production was greatly depressed by using the deoxygenation catalyst of Example 4, and almost 16% less feed carbon ended up as a paraffin product. Most of that depression came as a result of producing substantially less of the undesirable $C_{4-}$ paraffins.

A difference in coke deposition was also observed. Carbon removal from the Ni-modified ZSM-5 condensation catalyst was achieved through oxidative regeneration following the processing of the products produced using the deoxygenation catalyst from Example 6 and the deoxygenation catalyst from Example 4. The deoxygenation catalyst from Example 6 yielded on average around 2% of the carbon being fed as coke, while the deoxygenation catalyst from Example 4 yielded on average 5% of the carbon fed as coke. However, the difference in coke yield did not translate to a difference in short term catalyst deactivation. Due to the nature of the products produced by the deoxygenation catalyst from Example 4 and Example 6, both catalyst systems resulted in a 48 hour cycle before requiring regeneration to recover catalyst activity even though coke production was slightly different between the catalyst systems. As a result, the oxygenate product of the deoxygenation catalyst of Example 4 produces a tolerable amount of coke.

TABLE 12

Impact of feed on product composition.

| | | Catalyst | |
|---|---|---|---|
| | | Example 6 | Example 4 |
| Product Comp. | $CO + CO_2$ | 3.01 | 4.03 |
| (% CF) | $C_{4-}$ Paraffins | 15.72 | 3.58 |
| | $C_{5+}$ Paraffins | 7.51 | 3.89 |
| | $C_6 + C_7$ Aromatics | 15.84 | 14.33 |
| | $C_8$ Aromatics | 20.70 | 21.31 |
| | $C_9$ Aromatics | 16.44 | 18.93 |
| | $C_{10+}$ Aromatics | 6.96 | 8.47 |
| | Olefins | 1.65 | 3.06 |
| | Naphthenes | 4.04 | 1.88 |
| | Polynuclear Aromatics | 3.81 | 7.48 |
| | Oxygenates | 0.40 | 1.15 |
| | Total Aromatics | 59.94 | 63.04 |

In accord with the feed study from Example 1, Example 8 demonstrates the advantage of using certain mixtures of oxygenates to produce a high yield of aromatic hydrocarbons while minimizing the yield of paraffins.

Example 9

Deoxygenation Catalyst Synthesis

A second tetrametallic deoxygenation catalyst containing 2 wt % Pd, 2 wt % Mo, 0.5 wt % Sn/W—$ZrO_2$ was prepared using incipient wetness techniques. An aqueous solution of 2 molar ammonium nitrate (Sigma Aldrich) with a volume equal to the incipient wetness volume of the tungstated tetragonal zirconia (Norpro) to be impregnated and containing 1.186 g of tin (IV) chloride pentahydrate (Riedel de Haen) was added to 79.965 g of the catalyst carrier. The catalyst was dried at 130° C. for 2 hours. The catalyst was then calcined with air from ambient temperature to 200° C. at 2° C./min. From 200° C. to 220° C. the temperature ramp was slowed to 0.1° C./min. Finally, the temperature ramp rate was increased to 2° C./min from 220° C. to 400° C. Once the desired temperature was reached, the catalyst was soaked in air for an additional 6 hours. An aqueous solution of 2 molar ammonium nitrate (Sigma Aldrich) with a volume equal to the incipient wetness volume for the catalyst to be impregnated and containing 3.001 g of ammonium molybdate tetrahydrate (Sigma Aldrich) was added to the calcined catalyst. The catalyst was dried at 130° C. for 2 hours. An aqueous solution of 2 molar ammonium nitrate (Sigma Aldrich) with a volume equal to the incipient wetness volume for the catalyst to be impregnated and containing 4.105 g of palladium (II) nitrate hydrate (Alfa Aesar) was added to the calcined catalyst. The catalyst was dried at 130° C. for 2 hours. The catalyst was then calcined with air from ambient temperature to 200° C. at 2° C./min. From 200° C. to 220° C. the temperature ramp was slowed to 0.1° C./min. Finally, the temperature ramp rate was increased to 2° C./min from 220° C. to 400° C. Once the desired temperature was reached, the catalyst was soaked in air for an additional 6 hours.

Example 10

Production of Oxygenates

The deoxygenation catalysts from Example 9 and Example 4 were used to produce a mixture of oxygenated hydrocarbons for downstream processing across a Ni-modified ZSM-5 condensation catalyst. The reactor system is shown in FIG. 2. The deoxygenation catalyst from Example 9 was loaded as an 11.5 inch packed bed in a 1 inch outer diameter Inconel reactor. Before feed was introduced, the catalyst was reduced in-situ. The conditions were set at a temperature profile of 185-270° C., 1050 psig, a weight hourly space velocity (WHSV) of 0.5 grams of sugars per gram of catalyst per hour, a hydrogen co-feed of approximately 2 moles $H_2$ per 1 mole carbon fed, and an aqueous recycle ratio of 4 mass flow rate aqueous recycle to 1 mass flow rate feed. The feed was composed of 45 wt % glucose, 15 wt % xylose, and 40 wt % water with approximately 1000 ppm of propionic acid to prevent bacterial growth.

The catalyst defined in Example 4 was loaded as a 10 inch packed bed in a 1 inch outer diameter Inconel reactor. Before feed was introduced, the catalyst was reduced in-situ. The conditions were set at a temperature profile of 175-270° C., 1050 psig, a weight hourly space velocity (WHSV) of 0.4 grams of sugars per gram of catalyst per hour, a hydrogen co-feed of approximately 2 moles $H_2$ per 1 mole carbon fed, and an aqueous recycle ratio of 1 mass flow rate aqueous recycle to 1 mass flow rate feed. The feed was composed of 45 wt % glucose, 15 wt % xylose, and 40 wt % water with approximately 1000 ppm of propionic acid to prevent bacterial growth.

Table 13 shows the different product profiles for each deoxygenation catalyst. The catalyst from Example 9 results in a further extent of deoxygenation as shown by increased production of paraffin and monooxygenate species. The catalyst from Example 4, on the other hand, produces hydrocarbons with more oxygen as is highlighted by the production of dioxygenate and unidentified aqueous species.

TABLE 13

Deoxygenation product composition.

| | | Catalyst | |
|---|---|---|---|
| | | Example 9 | Example 4 |
| Product Comp. (% CF) | $CO + CO_2$ | 1.75 | 1.05 |
| | Paraffins | 10.71 | 0.23 |
| | Monooxygenates | 44.15 | 9.16 |
| | Dioxygenates | 9.95 | 35.59 |
| | Unidentified Aqueous | 18.90 | 49.77 |
| | Polyoxygenates | 0.37 | 1.78 |

Table 14 shows a more detailed breakdown of the product composition. The catalyst from Example 9 produces primarily alcohol and cyclic ether monooxygenates. In contrast, the catalyst of Example 4 produces primarily diol and unidentified aqueous compounds, which are believed to be di- and poly-oxygenates.

TABLE 14

Detailed product composition.

| | | Catalyst | |
|---|---|---|---|
| | | Example 9 | Example 4 |
| Product Comp. (% CF) | $CO + CO_2$ | 1.75 | 1.05 |
| | $C_{4-}$ Paraffins | 2.27 | 0.03 |
| | $C_{5+}$ Paraffins | 8.43 | 0.2 |
| | Alcohols | 19.81 | 3.17 |
| | Ketones | 1.83 | 1.73 |
| | Cyclic Ethers | 21.36 | 5.63 |
| | Cyclic Ketones | 1.14 | 0.07 |
| | Hydroxyketones + Diones | 0.57 | 1.44 |
| | Diols | 7.32 | 33.46 |
| | Acids | 2.06 | 0.67 |
| | Unidentified Aqueous | 18.90 | 49.77 |
| | Polyoxygenates | 0.37 | 1.78 |

Table 15 shows the carbon number breakdown of the identified carbon species in the product. The catalyst from Example 9 maintains the carbon backbone of the sugar feed and produces a small amount of longer chain compounds. In contrast, the catalyst of Example 4 produces shorter chain molecules, primarily in the $C_2$-$C_4$ range.

TABLE 15

Carbon number breakdown.

| | | Catalyst | |
|---|---|---|---|
| | | Example 9 | Example 4 |
| Product Comp. (% CF) | $C_1$ | 0.04 | 0.40 |
| | $C_2$ | 3.14 | 5.75 |
| | $C_3$ | 10.81 | 23.76 |
| | $C_4$ | 5.16 | 7.64 |
| | $C_5$ | 11.04 | 4.65 |

TABLE 15-continued

Carbon number breakdown.

| | Catalyst | |
|---|---|---|
| | Example 9 | Example 4 |
| $C_6$ | 34.36 | 4.67 |
| $C_7$ | 1.06 | 0.53 |
| $C_8$ | 1.45 | 0.00 |
| $C_9$ | 1.22 | 0.00 |
| $C_{10}$ | 0.46 | 0.00 |
| $C_{11}$ | 0.18 | 0.00 |
| $C_{12}$ | 0.29 | 0.00 |

Collectively, Table 13 through Table 15 show that the product compositions are different. The products of the deoxygenation catalyst of Example 4 tend to be oxygenated compounds having 2 to 4 carbon atoms and 2 or 3 oxygen atoms. Molecules of this type often have $H:C_{eff}$ ratios approximately between 0.5 and 1.5. As a result, the product composition of the catalyst of Example 4 has a lower $H:C_{eff}$ than the catalyst of Example 9.

Example 11

Production of Aromatic Molecules

Figure 4:
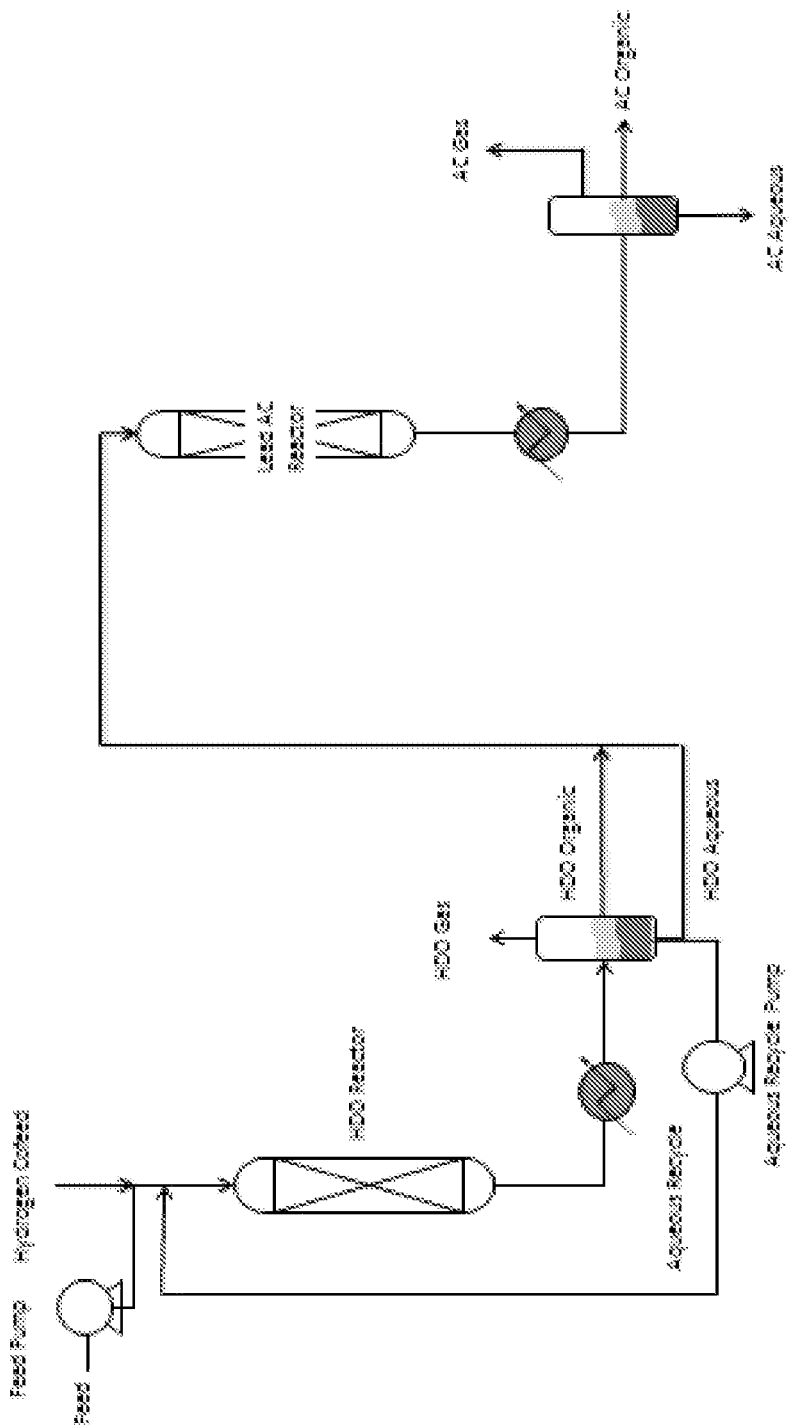
FIG. 4 is an exemplary process flow diagram for converting oxygenated hydrocarbons to liquid fuels and chemicals, including a deoxygenation reactor, an aqueous recycle stream, and a condensation reactor.
Figure 5:
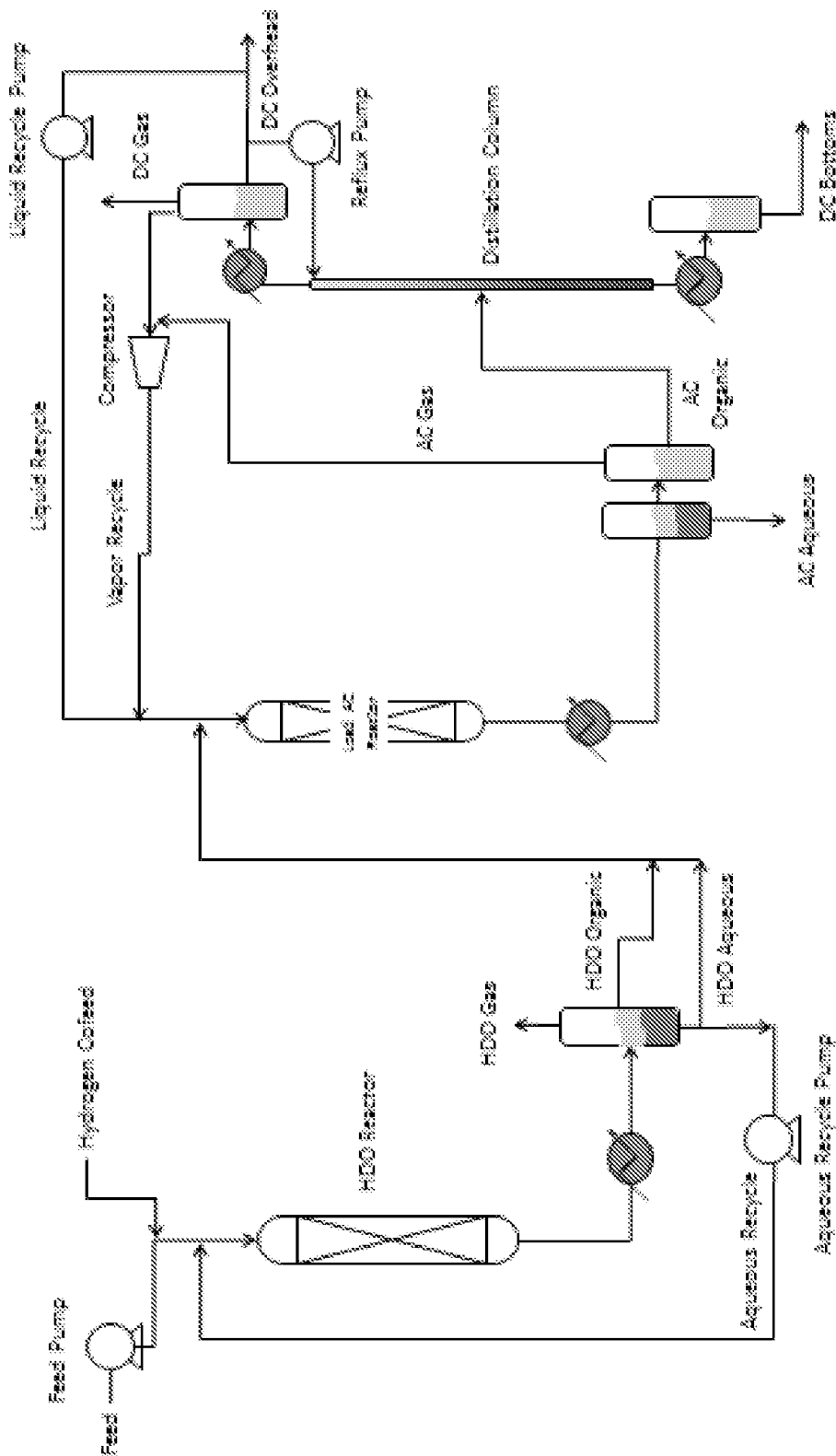
FIG. 5 is an exemplary process flow diagram for converting oxygenated hydrocarbons to liquid fuels and chemicals, including a deoxygenation reactor, an aqueous recycle stream, a condensation reactor, a vapor phase recycle stream, and a liquid phase (e.g., distillation column overhead product) recycle stream.

The products from Example 10 were processed downstream across a Ni-modified ZSM-5 condensation catalyst to evaluate the hydrocarbon yield and selectivity, short term catalyst deactivation, and process operability. The reactor system is shown in FIG. 4, and included a Ni-modified ZSM-5 condensation catalyst loaded as a 12 inch packed bed in a 1 inch outer diameter Inconel reactor. The conditions were set at 350° C., 100 psig, and a weight hourly space velocity (WHSV) of 0.5 grams of sugars per gram of catalyst per hour.

As a comparison, the products from the deoxygenation catalyst from Example 4 were also processed across a Ni-modified ZSM-5 condensation catalyst loaded as a 12 inch packed bed in a 1 inch outer diameter Inconel reactor. The conditions were set at 375° C., 100 psig, and a weight hourly space velocity (WHSV) of 0.4 grams of sugars per gram of catalyst per hour.

Table 16 shows the impact of the different oxygenate feeds on the hydrocarbon product yield and selectivity. The mixture of oxygenates produced using the deoxygenation catalyst of Example 4 increased the aromatics yield and decreased the paraffin yield when compared against the mixture of oxygenates producing using the deoxygenation catalyst of Example 9. Most notably, the paraffin production was greatly depressed using the oxygenate mixture from the catalyst of Example 4, with almost 17% less feed carbon ending up as a paraffin product. Most of that depression came as a result of producing substantially less of the undesirable $C_{4-}$ paraffins.

A difference in coke deposition was also observed. Carbon removal from the Ni-modified ZSM-5 condensation catalyst was achieved through oxidative regeneration following the processing of oxygenate mixtures from the Example 9 deoxygenation catalyst and the Example 4 deoxygenation catalyst. The mixture of oxygenations from the Example 9 deoxygenation catalyst yielded on average around 2% of the carbon being fed as coke while the mixture of oxygenates from the Example 4 deoxygenation catalyst yielded on average 5% of the carbon fed as coke. However, the difference in coke yield did not translate to a difference in short term catalyst deactivation. Due to the nature of the products produced by the deoxygenation catalyst from Example 4, both catalyst systems resulted in a 24 hour cycle before requiring regeneration to recover catalyst activity. As a result, the mixture of oxygenates produced using the deoxygenation catalyst of Example 4 produces a tolerable amount of coke.

TABLE 16

Impact of feed on product composition.

| | | Catalyst | |
|---|---|---|---|
| | | Example 9 | Example 4 |
| Product Comp. (% CF) | $CO + CO_2$ | 5.64 | 4.03 |
| | $C_{4-}$ Paraffins | 14.61 | 3.58 |
| | $C_{5+}$ Paraffins | 9.66 | 3.89 |
| | $C_6 + C_7$ Aromatics | 13.86 | 14.33 |
| | $C_8$ Aromatics | 17.78 | 21.31 |
| | $C_9$ Aromatics | 11.39 | 18.93 |
| | $C_{10}+$ Aromatics | 5.15 | 8.47 |
| | Olefins | 2.15 | 3.06 |
| | Naphthenes | 2.31 | 1.88 |
| | Polynuclear Aromatics | 3.42 | 7.48 |
| | Oxygenates | 0.47 | 1.15 |
| | Total Aromatics | 48.18 | 63.04 |

Example 12

Production of Oxygenates

The deoxygenation catalyst from Example 4 was tested at two different aqueous recycle ratios to examine its impact on feed conversion and product selectivity. The reactor system is shown in FIG. 2. The deoxygenation catalyst was loaded as a 10 inch packed bed in a 1 inch outer diameter Inconel reactor. The conditions for the aqueous recycle ratio of 1 mass flow rate aqueous recycle to 1 mass flow rate feed were set at 175-270° C., 1050 psig, a weight hourly space velocity (WHSV) of 0.4 grams of sugars per gram of catalyst per hour, and a hydrogen co-feed of approximately 2 moles $H_2$ per 1 mole carbon fed. The feed was composed of 45 wt/glucose, 15 wt % xylose, and 40 wt % water with approximately 1000 ppm of propionic acid to prevent bacterial growth. The conditions for the aqueous recycle ratio of 4 mass flow rate aqueous recycle to 1 mass flow rate feed were set at 160-285° C., 1050 psig, a weight hourly space velocity (WHSV) of 0.4 grams of sugars per gram of catalyst per hour, and a hydrogen co-feed of approximately 2 moles $H_2$ per 1 mole carbon fed. The feed was the same.

As is shown in Table 17, all of the sugars were converted in both recycle ratio cases. As recycle ratio was adjusted, a very minor shift in product selectivity is observed. In the case of the 4:1 aqueous recycle ratio slightly more alcohols are being produced. However, the impact of aqueous recycle ratio is minimal as the primary products, diols and unidentified aqueous, are at nearly equivalent levels.

TABLE 17

Product composition as a function of recycle ratio.

| | | Recycle Ratio | |
|---|---|---|---|
| | | 1:1 | 4:1 |
| Product Comp. (% CF) | $C_{4-}$Paraffins | 0.03 | 0.35 |
| | $C_{5+}$Paraffins | 0.20 | 0.59 |

TABLE 17-continued

Product composition as a function of recycle ratio.

|  | Recycle Ratio | |
| --- | --- | --- |
|  | 1:1 | 4:1 |
| Alcohols | 3.17 | 9.09 |
| Ketones | 1.73 | 3.14 |
| Cyclic Ethers | 5.63 | 6.04 |
| Hydroxy Ketones | 1.40 | 2.68 |
| Diols | 33.46 | 25.81 |
| Triols | 0.94 | 1.75 |
| Acids | 0.67 | 1.49 |
| Unidentified Aqueous | 49.77 | 40.18 |
| Sugar Alcohols | 0.78 | 2.34 |
| Sugars | 0.00 | 0.00 |

Examples 13-25

Example 13 through Example 25 describe the preparation of catalytic supports for use in accordance with the present invention. These materials (e.g., mesoporous alumina and/or mixed oxides) possess a BET surface area of less than 200 m$^2$/gram, more preferably less than 150 m$^2$/gram.

Example 13 B

A measured amount of a Boric Acid (Alfa Aesar) was added to a beaker containing 75 g of pseudoboehmite powder such that the Boron contributed 8% of the weight on a pseudoboehmite basis. The salts were admixed for ~5 minutes after which 80 mL of a 2% HNO3 solution (at ~70° C.) was added. Upon addition of the aforementioned solution to the mixed solids, gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 14 Cr

A measured amount of a Chromium Nitrate (Alfa Aesar) was added to a beaker containing 75 g of pseudoboehmite powder such that the Chromium contributed 8% of the weight on a pseudoboehmite basis. The salts were admixed for ~5 minutes after which 80 mL of a 2% HNO3 solution (at ~70° C.) was added. Upon addition of the aforementioned solution to the mixed solids, gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 15 Ce

Seventy five grams of a pseudoboehmite (Sasol) was added to a beaker. To this beaker a 150 mL solution containing 20.25 g of Cerium Nitrate (Aldrich) was added. The resulting slurry was stirred until gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 16 Co

Seventy five grams of a pseudoboehmite (Sasol) was added to a beaker. To this beaker a 150 mL solution containing 32.28 g of Cobalt(II) Nitrate (Alfa Aesar) was added. The resulting slurry was stirred until gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 17 Cu

Seventy five grams of a pseudoboehmite (Sasol) was added to a beaker. To this beaker a 150 mL solution containing 24.91 g of Copper Nitrate (Acros) was added. The resulting slurry was stirred until gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 18 Fe$_a$

Seventy five grams of a pseudoboehmite (Sasol) was added to a beaker. To this beaker a 150 mL solution containing 47.27 g of Iron Nitrate (Acros) was added. The resulting slurry was stirred until gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 19 Fe$_b$

Seventy five grams of a pseudoboehmite (Sasol) was added to a beaker. To this beaker a 150 mL solution containing 11.82 g of Iron Nitrate (Acros) was added. The resulting slurry was stirred until gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 20 Mg

Seventy five grams of a pseudoboehmite (Sasol) was added to a beaker. To this beaker a 150 mL solution containing 38.648 g of Magnesium Nitrate (Sigma Aldrich) was added followed by the addition of 2 mL of a 10% nitric acid solution and 0.5 g of hydroxyethyl cellulose (Fluka). The resulting slurry was stirred until gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 21 Mo

A measured amount of a Molybdic Acid (Sigma Aldrich) was added to a beaker containing 75 g of pseudoboehmite powder such that the Molybdenum contributed 8% of the weight on a pseudoboehmite basis. The salts were admixed for ~5 minutes after which 80 mL of a 2% HNO3 solution (at ~70° C.) was added. Upon addition of the aforementioned solution to the mixed solids, gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 22 Nb

A measured amount of a Niobium Chloride (Alfa Aesar) was added to a beaker containing 75 g of pseudoboehmite powder such that the Niobium contributed 8% of the weight on a pseudoboehmite basis. The salts were admixed for ~5 minutes after which 80 mL of a 2% HNO3 solution (at ~70° C.) was added. Upon addition of the aforementioned solution to the mixed solids, gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 23 Theta-AlO₃

To a beaker was added 750 g of pseudoboehmite (Sasol). The pseudoboehmite was diluted to 1800 mL with deionized water and the slurry was mixed for ~5 minutes. 22.5 g of hydroxyl ethyl cellulose was then added along with 20 mL of 10% HNO3. Upon addition of the aforementioned solution to the mixed solids, gelation occurred. The material was transferred to a 130° C. static oven and allowed to dry overnight. Calcination followed in a muffle furnace equipped with an air sweep gas flowing 10 cfm while ramping 2° C./min to 10000 and holding for 4 hours.

Example 24 W

A measured amount of a Tungsten Oxide (Alfa Aesar) was added to a beaker containing 75 g of pseudoboehmite powder such that the Tungsten Oxide contributed 8% of the weight on a pseudoboehmite basis. The salts were admixed for ~5 minutes after which 80 mL of a 2% HNO3 solution (at ~70° C.) was added. Upon addition of the aforementioned solution to the mixed solids, gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 25 Zr

Seventy five grams of a pseudoboehmite (Sasol) was added to a beaker. To this beaker a 150 mL solution containing 16.553 g of zirconyl nitrate (Sigma Aldrich) was added. The resulting slurry was stirred until gelation occurred. The material was transferred to a 130° C. static oven and allowed to dry overnight. Calcination followed in a muffle furnace equipped with an air sweep gas flowing 10 cfm while ramping 2° C./min to 1000° C. and holding for 4 hours.

Example 26

Support Properties

The surface area, pore diameter, and pore volume for the catalytic supports described in Example 13 through Example 25 are summarized in Table 18. The sample labeled NoproAl₂O₃ is commercially available from Saint-Gobain Norpro.

TABLE 18

Catalyst Support Properties

| Sample | Surface Area (m²/g) | Pore Diameter (Å) | Pore Vol. (cc/g) |
|---|---|---|---|
| B | 25 | 285 | 0.09 |
| Ce | 48.7 | 284 | 0.35 |
| Co | 40.1 | 169 | 0.15 |
| Cr | 52 | 288 | 0.28 |
| Cu | 52 | 288 | 0.28 |
| Fe$_a$ | 4.6 | 310 | 0.01 |
| Fe$_b$ | 25 | 240 | 0.10 |
| Mg | 49 | 199 | 0.24 |
| Mo | 14.5 | 176 | 0.32 |
| Nb | 53 | 286 | 0.3 |
| Theta-Al2O3 | 63.1 | 286 | 0.41 |
| W | 22 | 171 | 0.06 |
| Zr | 63.9 | 224 | 0.36 |
| NorproAl2O3 | 71.9 | 169 | 0.30 |

Example 27

Modified Supports

Ni was added to the supports in Example 13, Example 15, Example 18, Example 19, Example 23, and Example 25, and the catalysts were used to produce a mixture of oxygenates according to the present invention. Using the reactor system shown in FIG. 1, 12 grams of catalyst was loaded as packed bed in a ½ inch outer diameter Inconel reactor. Before feed was introduced, the catalyst was reduced using hydrogen at a space velocity of 700 hr⁻¹, a 2 hour temperature gradient to 400° C., followed by a 1 hour hydrogen soak. The conditions were set at 1050 psig, a weight hourly space velocity (WHSV) of 0.50 grams of sugars per gram of catalyst per hour, and a hydrogen co-feed of approximately 2 moles H₂ per 1 mole carbon fed. The feed was composed of 20 wt % glucose, 5% Xylose and 75 wt % water, with approximately 1000 ppm of propionic acid to prevent bacterial growth. The initial reaction temperature was set to a profile of 180-220° C., ramped over a period of 4 hours to 180-300° C., and held at that profile for a period of 3 hours, at which time the products were sampled.

As shown in Table 19, the various metal oxide modifications impact the catalyst selectivity ranging. Comparing the catalysts from Example 18 and Example 19, it can be seen that not only does the metal modification impact performance, but the amount of metal incorporated into the theta alumina structure is also important for product selectivity. Overall the metal modifications adjust selectivity from the base theta alumina support (Example 23) in a variety of ways from predominantly hydrogenation in the case of the catalyst from Example 18 to substantially more hydrodeoxygenation and decarbonylation from the catalysts of Example 25 and Example 15.

TABLE 19

| | | Product composition | | | | | |
|---|---|---|---|---|---|---|---|
| Catalyst | | Example 25 | Example 18 | Example 19 | Example 15 | Example 13 | Example 23 |
| Product | CO + $CO_2$ | 10.7 | 0.2 | 5.4 | 9.2 | 4.2 | 3.8 |
| Comp. | Paraffins | 41.0 | 0.5 | 37.1 | 40.7 | 20.7 | 1.1 |
| (% CF) | Monooxygenates | 27.1 | 0.3 | 23.8 | 20.4 | 17.1 | 5.7 |
| | Dioxygenates | 8.2 | 3.3 | 9.9 | 6.1 | 41.1 | 13.9 |
| | Un. Aqueous | 11.9 | 16.2 | 15.3 | 12.4 | 10.2 | 32.3 |
| | Polyoxygenates | 1.9 | 80.4 | 2.3 | 1.4 | 4.6 | 4.2 |

Example 28

Deoxygenation Catalyst Synthesis

A 50 mL solution containing 7.48 grams of Nickel (II) Nitrate hydrate (Alfa Aesar) and 0.71 grams Tin (IV) Chloride (Riedel de Haen) was added to 37 grams of tungstated zirconia (Norpro Saint-Gobain) in two separate equivalent aliquots. The solid was allowed to dry in between additions in a static oven at 120° C. for a period of 1 hour. After the second addition, the wetted solid was allowed to dry for a period of 3 hours in a static oven at 120° C. The solid was then transferred to a muffle furnace and calcined under flowing air (30 scfh). The calcination was accomplished by ramping the oven at 1.6° C./min until a final temperature of 400° C. was reached, after which the temperature was held for 6 hours.

Example 29

Deoxygenation Catalyst Synthesis

A solution 13 mL solution containing 0.53 grams of Tin (IV) Chloride pentahydrate (Riedel de Haen) and DI water was added to 28.04 grams of tungstated zirconia (Norpro Saint-Gobain) via incipient wetness technique. The resulting wetted solid was dried in a static oven at 120° C. for a period of 2 hours. After which the solid was removed and calcined in a muffle furnace equipped with an air sweep gas flowing 30 scfh. The calcination was accomplished by ramping the oven at 1.6° C./min until a final temperature of 400° C. was reached after which the temperature was held for 6 hours. The oven was allowed to cool, the solid removed and impregnated via incipient wetness technique with a 13 mL solution containing 1.03 grams of Ammonium Molybdate Tetrahydrate (Sigma Aldrich). The wetted solid was then dried and calcined according to the aforementioned procedure. Palladium impregnation was accomplished via addition of a 13 mL solution containing 1.41 grams of Palladium (II) Nitrate Hydrate (Alfa Aesar) via incipient wetness technique. The resulting solid was dried and calcined via aforementioned procedures.

Example 30

Production of Oxygenates

Figure 6:
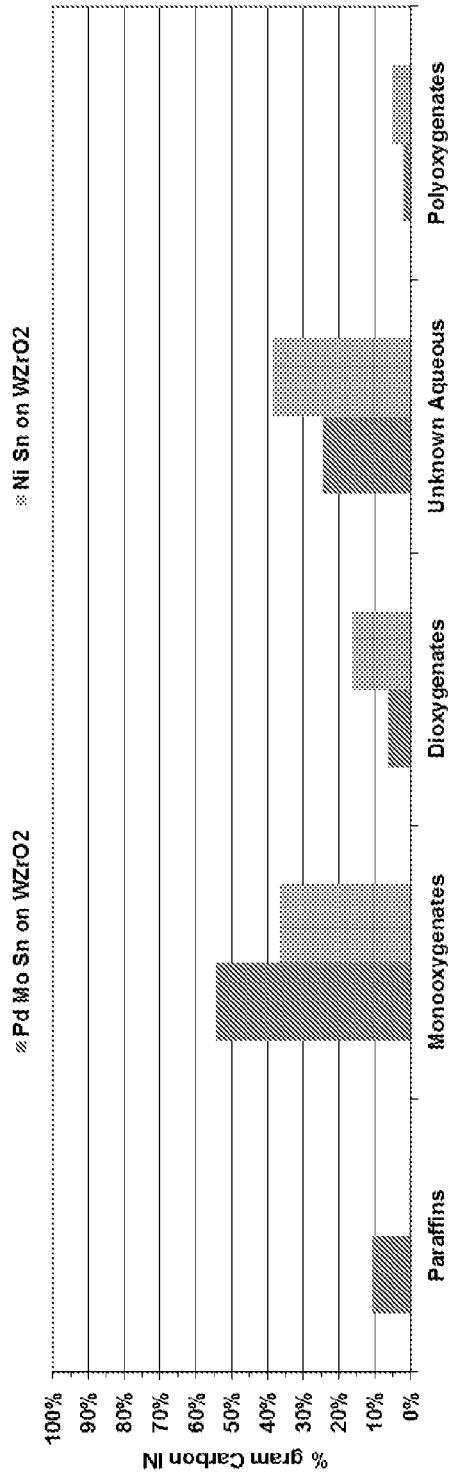
FIG. 6 is an exemplary product distribution illustrating the effect of the deoxygenation catalyst composition on the product profile. The catalyst compositions were 2% Pd 2% Mo 0.5% Sn on W—ZrO2 (reduced to 300° C.) and 4% Ni 1% Sn on W—ZrO2 (reduced to 300° C.).

Catalysts provided in Example 28 and Example 29 were tested in a reactor system configured in the process flow diagram in FIG. 1. The reactor temperature outlet was maintained at 270° C. The sugar feedstock was supplied at a rate of 1 gram sugar per 1 gram catalyst per hour. Reactor pressure was maintained at 1050 psig. The results of the testing are provided in FIG. 6.

Example 31

Deoxygenation Catalyst Synthesis

A solution 12 mL solution containing 5.691 grams of ammonium tungsten oxide hydrate (Alfa Aesar) and DI water was added to 26.021 grams of theta alumina (Norpro Saint-Gobain) via incipient wetness technique. The resulting wetted solid was dried in a static oven at 120° C. for a period of 2 hours. After which the solid was removed and calcined in a muffle furnace equipped with an air sweep gas flowing 30 scfh. The calcination was accomplished by ramping the oven at 1.6° C./min until a final temperature of 400° C. was reached after which the temperature was held for 6 hours. The oven was allowed to cool, the solid removed and impregnated via incipient wetness technique with a 12 mL solution containing 0.385 grams of Tin (IV) Chloride pentahydrate (Riedel de Haen). The wetted solid was then dried and calcined according to the aforementioned procedure. Molybdenum addition was accomplished via incipient wetness impregnation of the resulting solid with a 12 mL solution containing 0.975 grams of Ammonium Molybdate Tetrahydrate (Sigma Aldrich). The resulting solid was dried according to the aforementioned procedure followed by Palladium impregnation. Palladium impregnation was accomplished via addition of a 12 mL solution containing 1.333 grams of Palladium (II) Nitrate Hydrate (Alfa Aesar) via incipient wetness technique. The resulting solid was dried and calcined via aforementioned procedures.

Example 32

Deoxygenation Catalyst Synthesis

A solution 12 mL solution containing 5.834 grams of ammonium tungsten oxide hydrate (Alfa Aesar) and DI water was added to 26.652 grams of monoclinic zirconia (Norpro Saint-Gobain) via incipient wetness technique. The resulting wetted solid was dried in a static oven at 120° C. for a period of 2 hours. After which the solid was removed and calcined in a muffle furnace equipped with an air sweep gas flowing 30 scfh. The calcination was accomplished by ramping the oven at 1.6° C./min until a final temperature of 400° C. was reached after which the temperature was held for 6 hours. The oven was allowed to cool, the solid removed and impregnated via incipient wetness technique with a 12 mL solution containing 0.395 grams of Tin (IV) Chloride pentahydrate (Riedel de Haen). The wetted solid was then dried and calcined according to the aforementioned procedure. Molybdenum addition was accomplished via incipient wetness impregnation of the resulting solid with a 12 mL solution containing 1.000 grams of Ammonium Molybdate Tetrahydrate (Sigma Aldrich). The resulting solid was dried according to the aforementioned procedure followed by Palladium impregnation. Palladium impregnation was accomplished via addition of a 12 mL solution containing 1.367 grams of Palladium (II) Nitrate Hydrate (Alfa Aesar) via incipient wetness technique. The resulting solid was dried and calcined via aforementioned procedures.

Example 33

Production of Oxygenates

Catalysts provided in Example 31 and Example 32 were tested in a reactor system configured in the process flow diagram in FIG. 2. The reactor temperature outlet was maintained at 270° C. A 50 wt % 43 DE corn syrup (Food Ingredients, Inc.) that was passed over an ion exchange column and doped with 1000 ppm propionic acid feedstock was supplied at a rate of 1 gram feedstock per 1 gram catalyst per hour. Reactor pressure was maintained at 1050 psig and a recycle flow rate was also maintained at a mass ratio of 4:1 on a mass basis. The results of the testing are provided in FIG. 7.

Example 34

Production of Oxygenates

Figure 8:
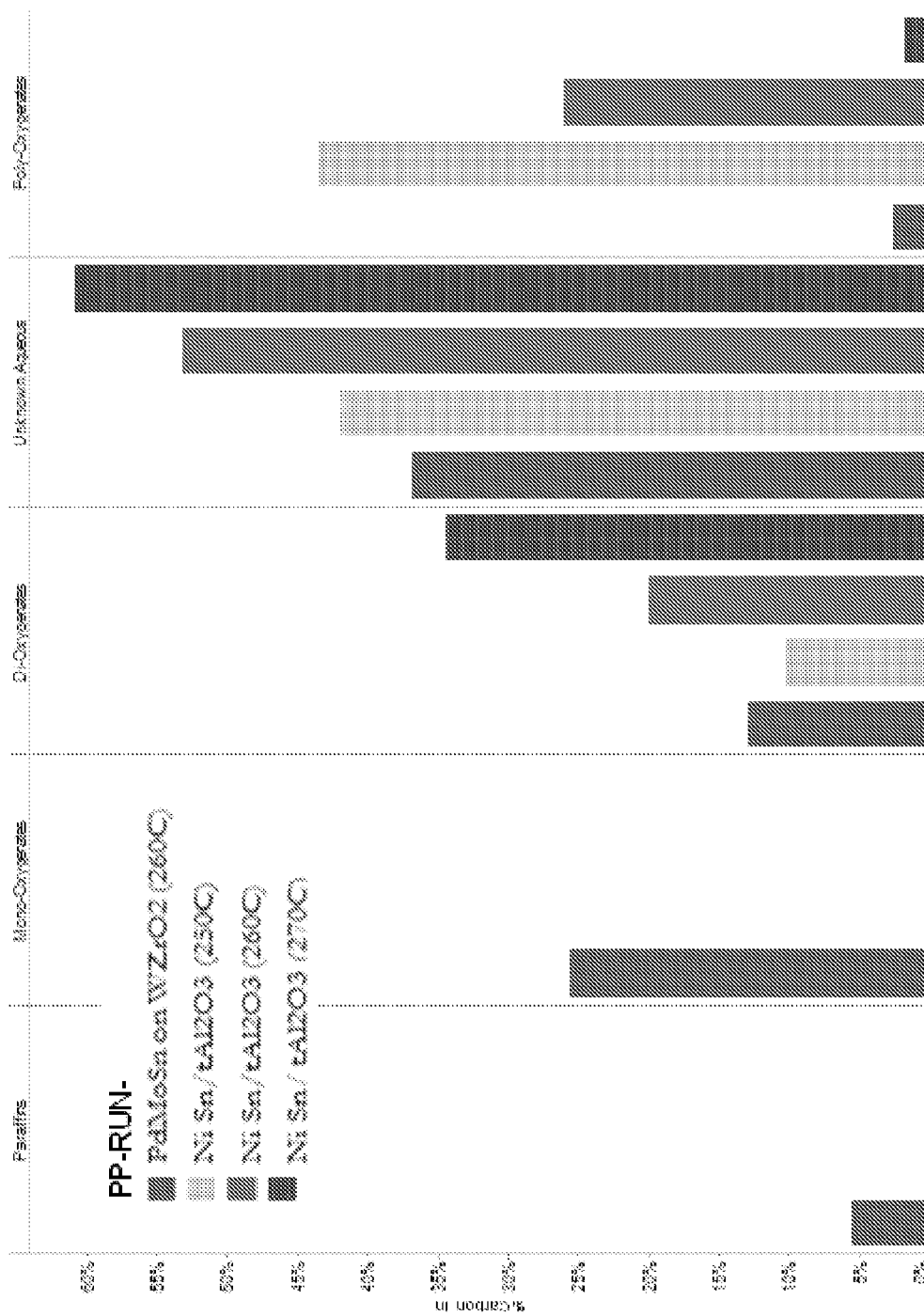
FIG. 8 is an exemplary product distribution (e.g., paraffins, dioxygenates, etc.) illustrating the effect of the deoxygenation catalyst composition and temperature on the product profile
Figure 9:
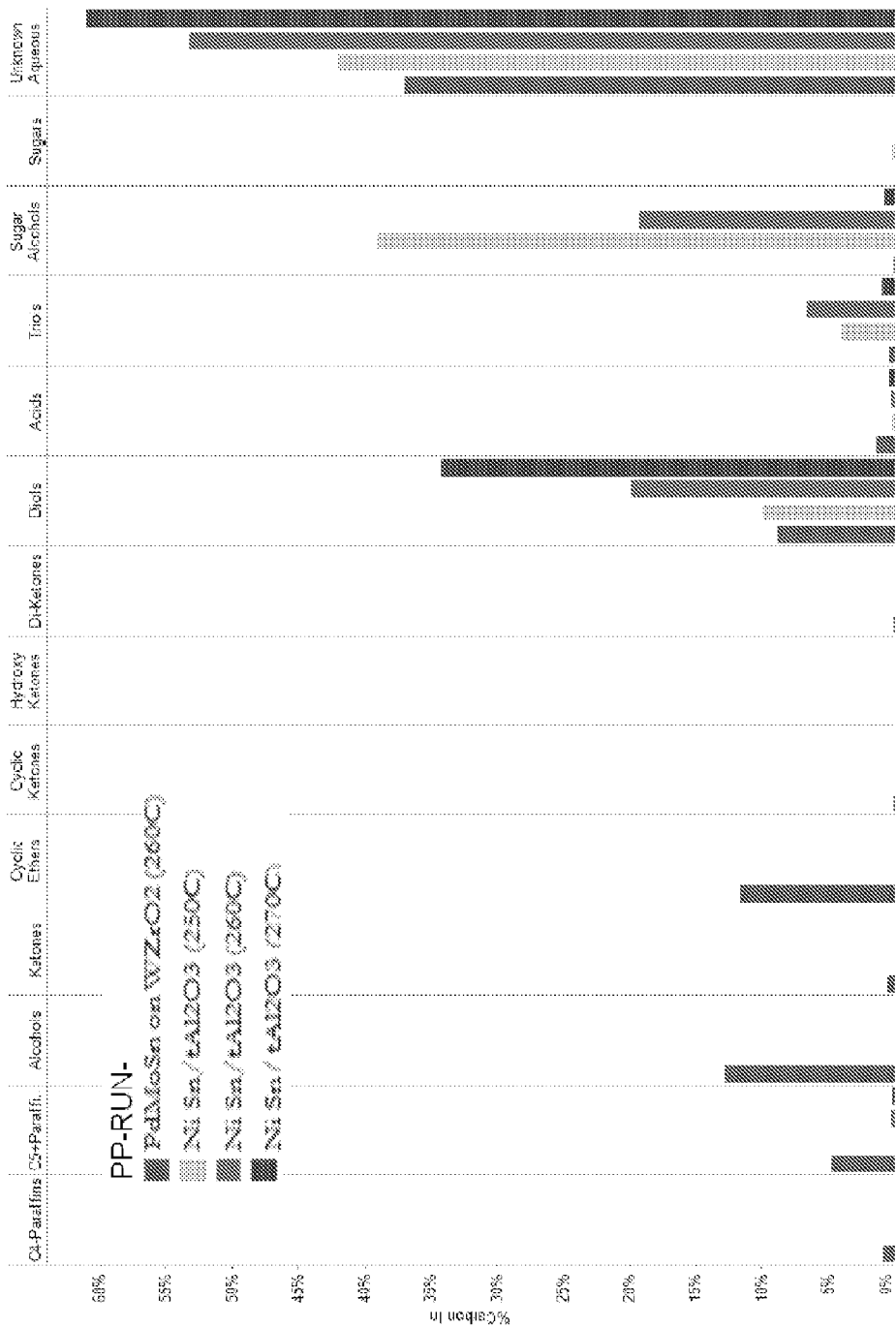
FIG. 9 is an exemplary product distribution (e.g., ketones, cyclic ethers, etc.) illustrating the effect of the deoxygenation catalyst composition and temperature on the product profile.

The two deoxygenation catalysts from Example 4 and Example 9 were tested in the reactors system illustrated by FIG. 2. A 50 wt % 43 DE corn syrup (Food Ingredients, Inc.) was passed over an ion exchange column and doped with 1000 ppm propionic acid feedstock before being supplied at a flow rate of 0.5 grams feedstock per gram catalyst per hour and the recycle rate was a 1:1 mass ratio. The inlet of the reactor was kept at 180° C. for both catalyst systems. The outlet temperature was intentionally modified as noted in FIG. 8 through FIG. 9 to examine selectivity of the NiSn catalyst.

Example 35

Synthesis of NiSn Alloy Catalysts

A NiSn alloy deoxygenation catalyst was prepared as follows. The multi-step synthesis involves (1) solvation, (2) impregnation of the support, (3) precipitation, (4) crystallization, and (5) reduction/activation. Table 20 contains a list of all reagents and their manufacturers that were used in the synthesis of the NiSn alloys.

TABLE 20

List of Reagents

| Reagent | Name | Manufacturer |
|---|---|---|
| 1 | Nickel(II) Chloride hydrate | Alfa Aesar |
| 2 | Tin(II) Chloride hydrate | Alfa Aesar |
| 3 | 2-Methoxyethanol (2ME) | Sigma Aldrich |
| 4 | Ethanol (denatured) | Columbus Chemical |
| 5 | Sodium Hydroxide | Fisher Scientific |
| 6 | Industrial Hydrogen | Air Gas |

Unsupported Alloy Synthesis:

A measured amount of reagents 1 and 2 were added to a round bottom flask equipped with a condenser. A solution containing deionized (DI) water, ethanol and, 2-Methoxyethanol (2ME) was added to the round bottom flask in the quantities detailed in Table 21. The reaction mixture was then heated to 50° C. for a period of 30 minutes to facilitate dissolution of the metal salts while stirring. Next, a 3M solution of NaOH was added drop-wise to the top of the condenser column to precipitate the corresponding metal hydroxides until a final pH of >10 was observed. For the crystallization step, the entire contents of the reaction mixture were emptied into a Teflon liner and loaded into a sealed autoclave; Parr instrument Company model 4566 (300 mL). The reactor was then heated to 150° C. over the course of 2 hours under autogeneous pressure. After being held at temperature for an additional period of 18 hours, the reactor was allowed to cool. Upon completion of the crystallization, the solids were recovered via vacuum filtration and washed with 3 equivalents (200 mL each) of DI water followed by drying in a static oven at 120° C. The dried solids were then ready for reduction during which they were loaded into a quartz reactor placed into a furnace. Under flowing hydrogen, the reactor was heated 2° C./min to a final temperature of 400° C. and held for a period of 4 hours.

TABLE 21

Detailed Quantities of Synthesis Reagents (unsupported alloys)

| Description | Ni(Cl)$_2$ (g) | Sn(Cl)$_2$ (g) | 2ME (g) | Ethanol (g) | DI water (g) |
|---|---|---|---|---|---|
| Ni3Sn2 | 13.690 | 8.670 | 33.43 | 16.65 | 10 |
| Ni3Sn1 | 17.117 | 5.416 | 33.42 | 16.60 | 10 |
| Ni3Sn4 | 10.478 | 12.459 | 27.83 | 13.84 | 10 |
| Ni | 15.206 | — | 33.38 | 16.62 | 10 |

Supported Alloy Synthesis:

The catalyst carriers used for the supported alloy preparation are listed in Table 22.

TABLE 22

Catalyst Carriers

| Description | Manufacturer | Product number |
|---|---|---|
| Theta alumina | Saint-Gobain Norpro | SA31145 |
| Alpha alumina | Saint-Gobain Norpro | SA5151 |
| Monoclinic Zirconia | Saint-Gobain Norpro | SZ31145 |
| Activated Carbon | Calgon | 206 CAT-P |

A measured amount of reagents 1 and 2 were added to a beaker, followed by a solution containing deionized (DI) water, ethanol and, 2-Methoxyethanol (2ME) at the quantities detailed in Table 23. The reaction mixture was then heated to 100° C. for a period of 10 minutes to facilitate dissolution of the metal salts while stirring. The solution was then added to a measured amount of catalyst carrier such that the incipient wetness of the carrier was achieved based on the volume of total solution. Next, a 3M solution of NaOH was added drop-wise to a Teflon liner loaded with the wetted solid. The addition of NaOH resulted in the precipitation of the corresponding metal hydroxides, which was ceased after a final pH of >10 was observed. For the crystallization step, the Teflon liner was loaded into a sealed autoclave, Parr instrument Company model 4566 (300 mL). The reactor was then heated to 150° C. over the course of 2 hours under autogeneous pressure. After being held at temperature for an additional period of 18 hours, the reactor was allowed to cool. Upon completion of the crystallization, the solids were recovered via vacuum filtration and washed with 3 equivalents (200 mL each) of DI water followed by drying in a static oven at 120° C. The dried solids were then loaded into a quartz reactor placed into a furnace. Under flowing hydrogen, the reactor was heated 2° C./min to a final temperature of 400° C. and held for a period of 4 hours.

TABLE 23

Detailed Quantities of Synthesis Reagents (supported alloys)

| Alloy | Carrier | Ni(Cl)$_2$ (g) | Sn(Cl)$_2$ (g) | 2ME (g) | Ethanol (g) | H$_2$O (g) | Carrier (g) |
|---|---|---|---|---|---|---|---|
| Ni$_3$Sn$_1$ | θ-Al$_2$O$_3$ | 6.849 | 2.167 | 4.147 | 8.245 | 3.8 | 22.000 |
| Ni$_3$Sn$_2$ | θ-Al$_2$O$_3$ | 6.846 | 4.337 | 3.326 | 6.881 | 2.665 | 21.080 |
| Ni$_3$Sn$_4$ | θ-Al$_2$O$_3$ | 6.846 | 8.666 | 3.322 | 6.681 | 4.4 | 22.000 |
| Ni$_3$Sn$_2$ | α-Al$_2$O$_3$ | 13.010 | 8.239 | 3.152 | 6.350 | 1.532 | 42.015 |
| Ni$_3$Sn$_2$ | Carbon | 6.850 | 4.337 | 1.670 | 3.345 | 3.081 | 22.581 |
| Ni$_3$Sn$_2$ | m-ZrO2 | 11.467 | 7.221 | 2.781 | 5.582 | 5.030 | 35.257 |

Example 36

Production of Oxygenates

The unsupported NiSn alloys were tested alongside a baseline supported 8% Ni 2% Sn/θ-Al$_2$O$_3$ catalyst in a batch service. The catalysts were reduced ex-situ before being loaded under water into a stirred tank reactor. The reduction conditions are shown in Table 24. All experiments were run with a 20% sorbitol feedstock. The experiments in Table 25 were run for a comparison between the various deoxygenation catalysts. The pressure listed is the target pressure at the end of the temperature ramp, but this actually varied somewhat depending on the activity of each individual catalyst. Each run was designed to have an equal amount of Ni loaded into the reactor based on the ICP results of the fresh catalyst.

TABLE 24

Stirred Tank Reduction Conditions

| Catalyst | Temperature (° C.) | H$_2$ Flow (mL/min) | Ramp (hr) | Soak (hr) |
|---|---|---|---|---|
| All catalysts | 450 | 250 | 4 | 2 |

TABLE 25

Stirred Tank Reaction Conditions

| Catalyst Formulation | 8% Ni 2% Sn/ θ-Al$_2$O$_3$ | Ni$_3$Sn$_1$ | Ni$_3$Sn$_2$ | Ni$_3$Sn$_4$ | Ni only | Ni3Sn2/ θ-Al$_2$O$_3$ |
|---|---|---|---|---|---|---|
| Catalyst Mass (g) | 10 | 2.44 | 3.08 | 4.85 | 1.52 | 28.05 |
| H$_2$ Pressure (psig) | 1050 | 1050 | 1050 | 1050 | 1050 | 1050 |
| Temp Ramp (° C./min) | 3 | 3 | 3 | 3 | 3 | 3 |
| Final Temp (° C.) | 250 | 250 | 250 | 250 | 250 | 250 |
| Soak Time (min) | 120 | 120 | 120 | 120 | 120 | 120 |

Figure 10:
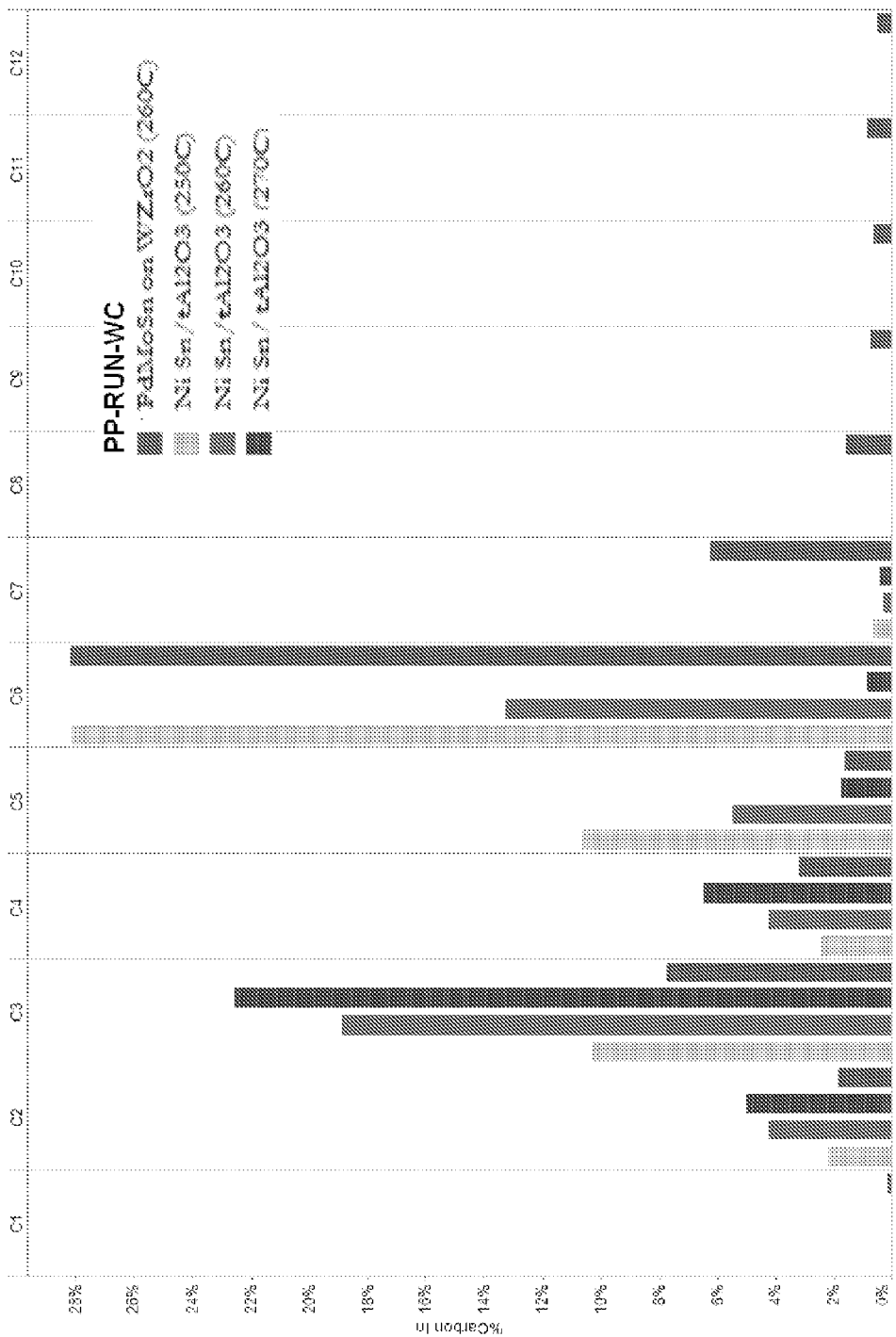
FIG. 10 is an exemplary carbon distribution of identified compounds illustrating the effect of the deoxygenation catalyst composition and temperature on the product profile.
Figure 11:
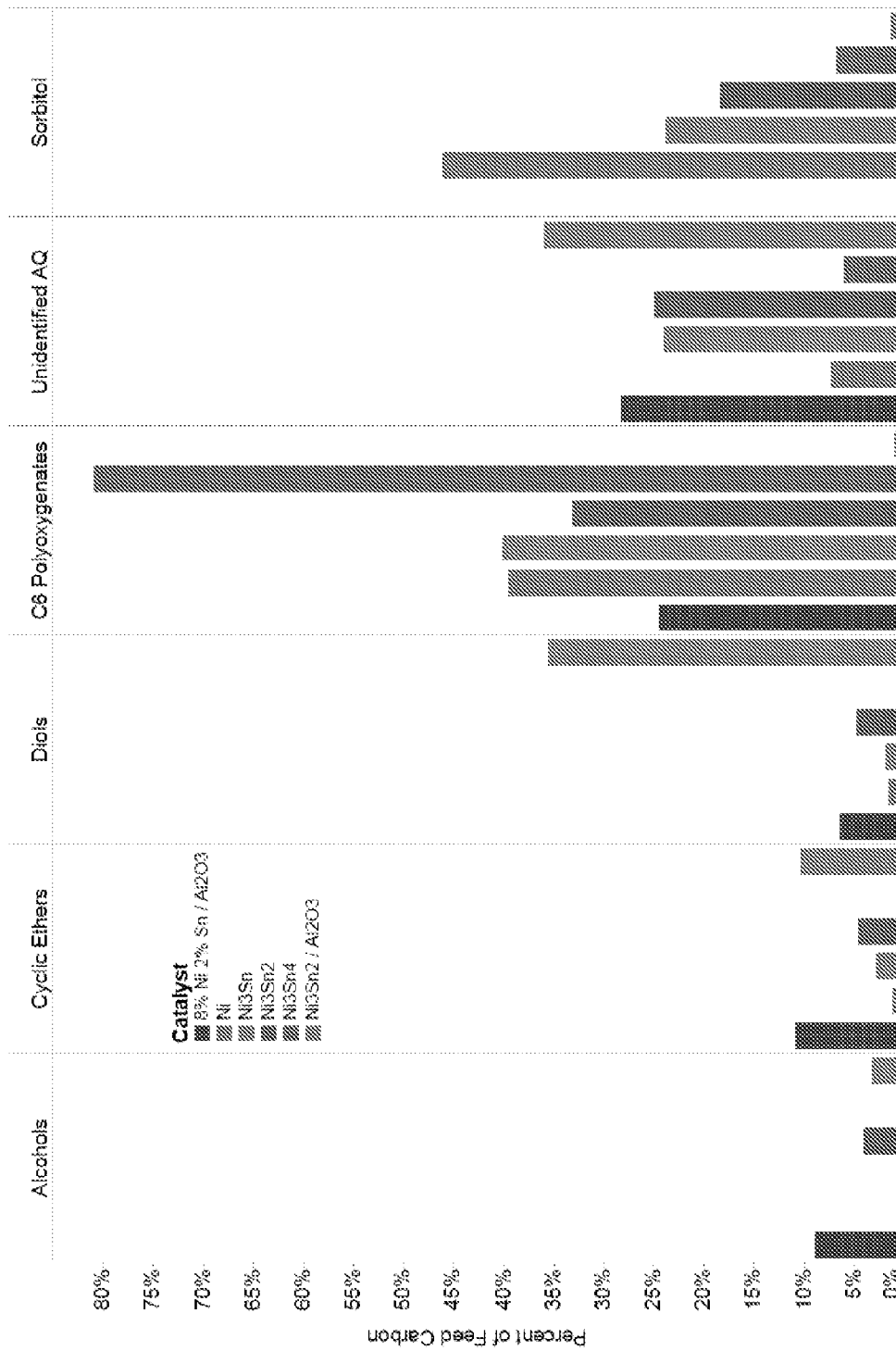
FIG. 11 is a comparison of oxygenated compounds generated with various catalysts containing Ni and Sn in a batch reactor.

A comparison of the products is shown in FIG. 10. It can be seen by comparing the unsupported catalysts that each alloy has different activity and selectivity. With conversion similar to a blank run with no catalyst, the Ni only material converted only about 55% of the sorbitol. Most of the identified products were sorbitan and isosorbide, which can be produced by thermal reactions alone. The Ni$_3$Sn alloy was more active, converting about 75% of the sorbitol, but did not show much of an increase in alcohol or diol products. The Ni$_3$Sn$_2$ alloy performed the best of the unsupported materials, converting over 80% of the sorbitol and producing about 5% of both diols and alcohols. The Ni$_3$Sn$_4$ alloy had different activity compared to the other alloy catalysts, and while it had over 90% conversion of sorbitol, almost all of the identified products were sorbitan and isosorbide, which are produced simply by dehydration reactions.

When comparing the activity of the unsupported alloys to the supported catalysts, it is clear that supporting the metals on θ-Al$_2$O$_3$ greatly increases the activity of the catalysts. By comparing the two supported catalysts to each other, it can be seen that the Ni$_3$Sn$_2$ alloy catalyst greatly outperforms the incipient wetness catalyst, specifically in diol production. The supported Ni$_3$Sn$_2$ catalyst also produced almost no sorbitan or isosorbide compared to over 20% for the incipient wetness catalyst.

Example 37

Production of Oxygenates

The supported NiSn alloy deoxygenation catalysts were further tested in a fixed bed reactor system. The catalysts were tested with isothermal conditions and at three different WHSV. The final weight check (WC) was done at the same conditions as the first to check for deactivation during the run. The reaction conditions are shown in Table 26.

TABLE 26

Reaction Conditions

| WC | Feed | HZ1 T (° C.) | HZ2 T (° C.) | HZ3 T (° C.) | HZ4 T (° C.) | P (psig) | WHSV (hr$^{-1}$) |
|---|---|---|---|---|---|---|---|
| 1 | 50% Sorbitol | 250 | 250 | 250 | 250 | 1050 | 0.5 |
| 2 | 50% Sorbitol | 250 | 250 | 250 | 250 | 1050 | 1 |
| 3 | 50% Sorbitol | 250 | 250 | 250 | 250 | 1050 | 1.5 |
| 4 | 50% Sorbitol | 250 | 250 | 250 | 250 | 1050 | 0.5 |

Figure 12:
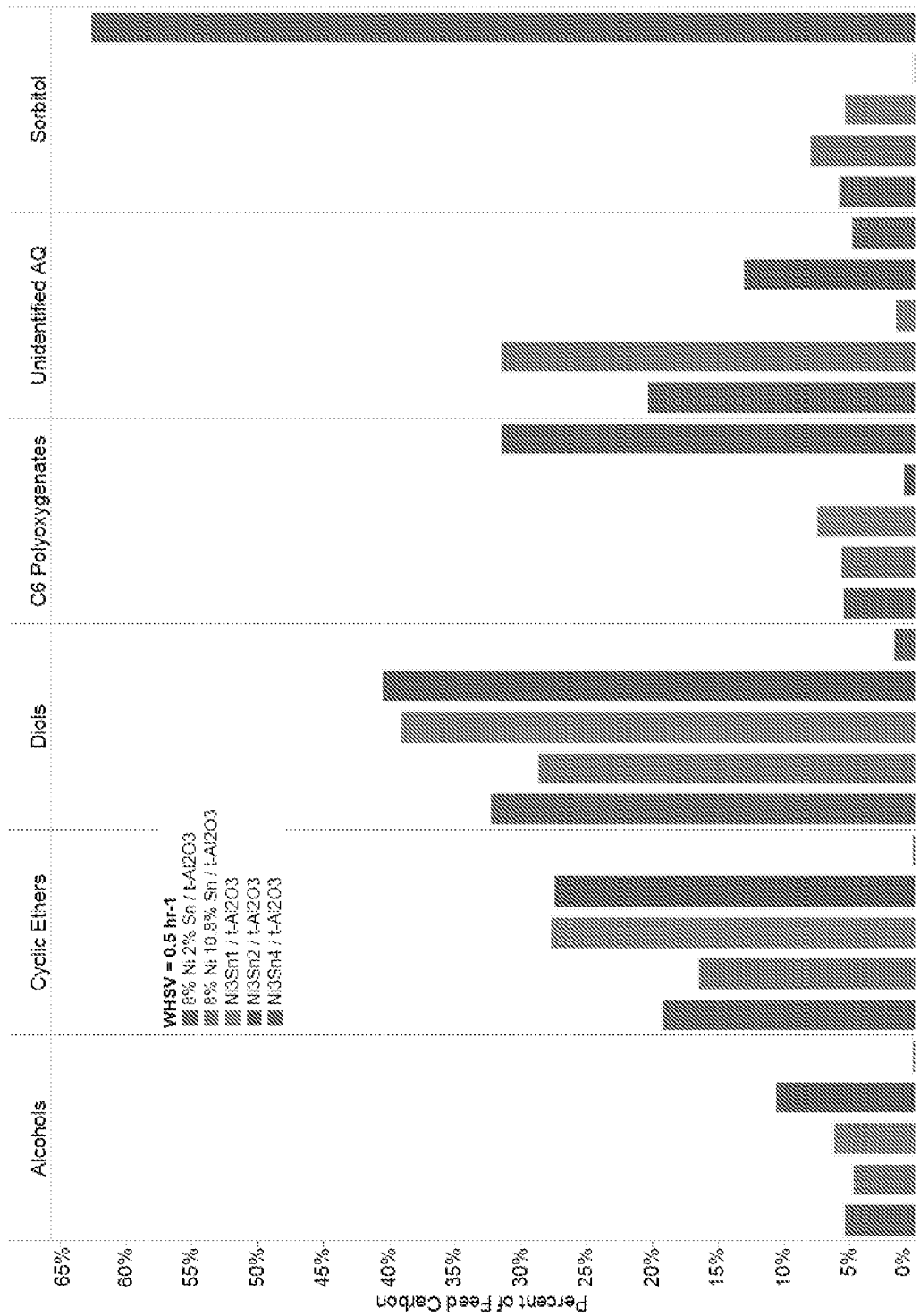
FIG. 12 is a comparison of oxygenated compounds generated with various catalysts containing Ni and Sn in a fixed bed reactor at a WHSV of 0.5 hr$^{-1}$.

FIG. 12 shows the results for the deoxygenation catalysts containing NiSn alloys supported on θ-Al$_2$O$_3$ compared to standard incipient wetness catalysts in a flow-through reactor system at WSHV=0.5 hr$^{-1}$. Similar trends to the unsupported catalysts can be observed. The Ni$_3$Sn and Ni$_3$Sn$_2$ alloys have similar product profiles to the incipient wetness catalysts and are more selective at producing diols. The supported Ni$_3$Sn$_4$ alloy is the lowest activity catalyst tested. Again, this catalyst only seems to catalyze dehydration reactions as the bulk of the identified products are isosorbide and sorbitan. At this WHSV, all catalysts except for the Ni$_3$Sn$_4$ alloy achieved nearly full conversion and thus, all of the product profiles were similar.

Figure 13:
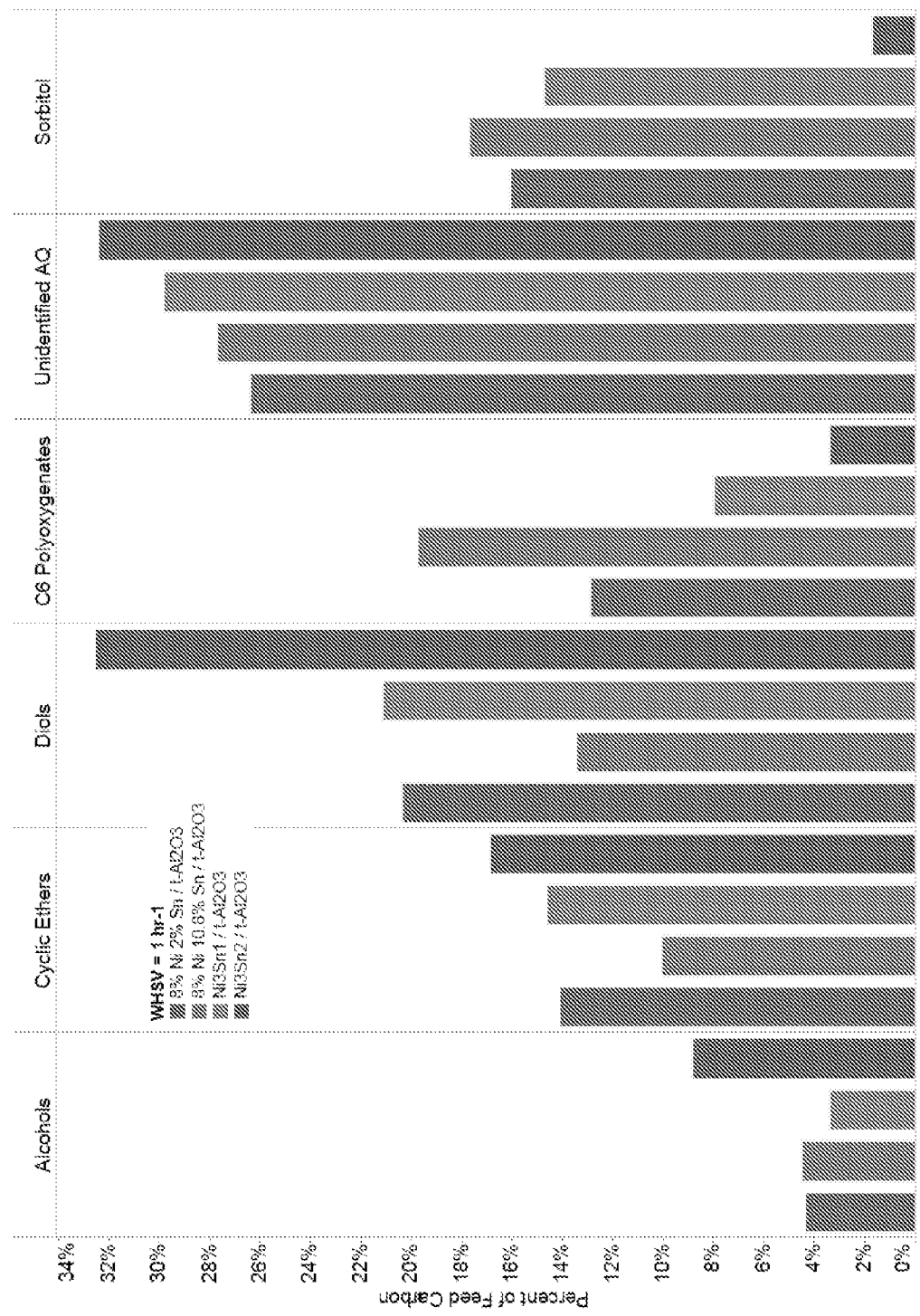
FIG. 13 is a comparison of oxygenated compounds generated with various catalysts containing Ni and Sn in a fixed bed reactor at a WHSV of 1.0 hr$^{-1}$.

FIG. 13 compares the performance of the supported NiSn alloy deoxygenation catalysts at WHSV=1 hr$^{-1}$. The Ni$_3$Sn$_4$ alloy was omitted from FIG. 12 because of low conversion and poor diol selectivity. At this WHSV, the Ni$_3$Sn$_2$ supported alloy is clearly the best performing catalyst. The Ni$_3$Sn$_2$ alloy maintained nearly full conversion of sorbitol while each of the other catalysts tested dropped to about 85% conversion. In addition, this catalyst converted over 30% of the feed carbon to diols, 1.5 times more than any other catalyst. In fact, the Ni$_3$Sn$_2$ catalyst at WHSV=1 hr$^{-1}$ performs almost identically to a 8% Ni 2% Sn/θ-Al$_2$O$_3$ catalyst at WHSV=0.5 hr$^{-1}$.

Figure 14:
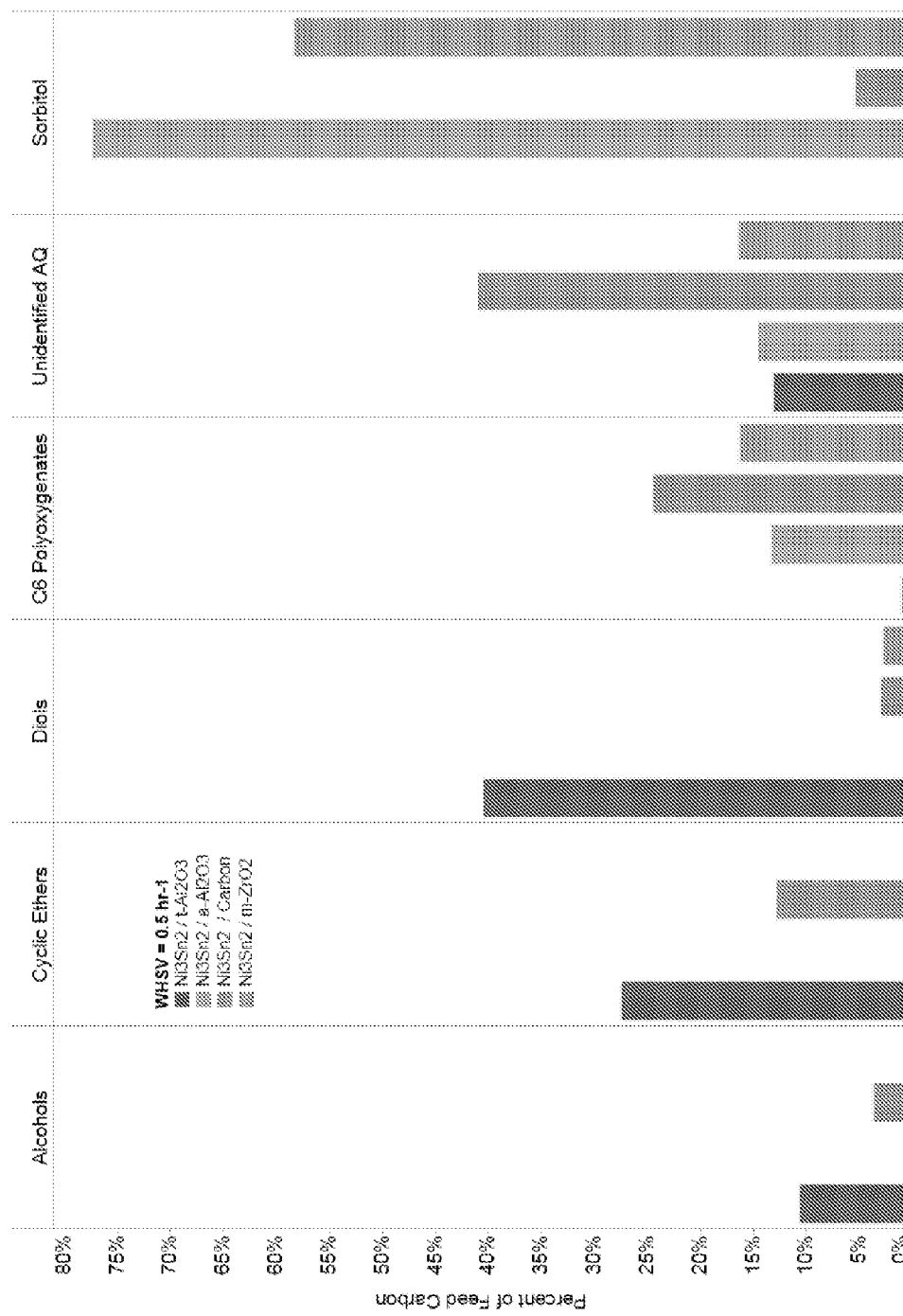
FIG. 14 is a comparison of oxygenated compounds generated with various catalysts containing $Ni_3Sn_2$ alloy catalyst on different supports.

In addition to θ-Al$_2$O$_3$, α-Al$_2$O$_3$, an activated carbon and monoclinic ZrO$_2$ were tested as supports for the Ni$_3$Sn$_2$ alloy, with the results shown in FIG. 14. Both α-Al$_2$O$_3$ and m-ZrO$_2$ performed much more poorly than the θ-Al$_2$O$_3$ supported material in terms of both activity and selectivity. Both catalysts had less than 50% conversion and nearly all of the identified products were isosorbide and sorbitan. The activated carbon supported Ni$_3$Sn$_2$ alloy did have approximately 95% conversion, although the catalyst had extremely low selectivity to retro-aldol condensation products. Of the materials tested, the θ-Al$_2$O$_3$ support is preferred for the present invention.

The invention claimed is:

1. A method for producing oxygenated compounds from oxygenated hydrocarbons, the method comprising:
   reacting an aqueous feedstock, the aqueous feedstock comprising water and one or more oxygenated hydrocarbons selected from the group consisting of, monosaccharides, disaccharides, oligosaccharides, polysaccharides, sugar alcohols, sugar degradation products, alditols, starches, organic acids, polyols, and mixtures thereof, with hydrogen in the presence of a catalyst comprising a metal selected from the group consisting of Ni and Pd, at least one metal selected from the group consisting of Mo and Sn, and a support, to produce a mixture of oxygenates,
   wherein the H:Ceff ratio of the mixture of oxygenates is greater than or equal to 0.5 and less than or equal to 1.7.

2. The method of claim 1, wherein the mixture of oxygenates has one or more attributes selected from the group consisting of (i) a % CF ratio greater than or equal to 0.5 of dioxygenates and polyoxygenates to monooxygenates, (ii) a % CF ratio greater than or equal to 0.5 of dioxygenates to monooxygenates, (iii) a % CF ratio greater than or equal to 1.0 of C2-4 oxygenates to C5-6 oxygenates, and (iv) the mixture of oxygenates further comprising alkanes and less than or equal to 10% CF alkanes.

3. A method for producing hydrocarbons, the method comprising:
   (a) reacting an aqueous feedstock, the aqueous feedstock comprising water and one or more oxygenated hydrocarbons selected from the group consisting of monosaccharides, disaccharides, oligosaccharides, polysaccharides, sugar alcohols, sugar degradation products, alditols, starches, organic acids, polyols, and mixtures thereof, with hydrogen in the presence of a catalyst comprising a metal selected from the group consisting of Ni and Pd, at least one metal selected from the group consisting of Mo and Sn, and a support, to produce a mixture of oxygenates and
   (b) reacting the mixture of oxygenates with a condensation catalyst to produce a mixture of hydrocarbons comprising C4+ alkanes and aryls,
   wherein the mixture of hydrocarbons comprises greater than or equal to 50% CF aryls and less than or equal to 20% CF C4+ alkanes.

4. The method of claim 3, wherein the H:Ceff ratio of the mixture of oxygenates is greater than or equal to 0.5 and less than or equal to 1.7.

5. The method of claim 3, wherein the mixture of oxygenates has one or more attributes selected from the group consisting of (i) a % CF ratio greater than or equal to 0.5 of dioxygenates and polyoxygenates to monooxygenates, (ii) a % CF ratio greater than or equal to 0.5 of dioxygenates to monooxygenates, (iii) a % CF ratio greater than or equal to 1.0 of C2-4 oxygenates to C5-6 oxygenates, and (iv) the mixture of oxygenates further comprising alkanes and less than or equal to 10% CF alkanes.

6. The method of claim 1, wherein the catalyst comprises Pd, Mo, and Sn on a crystalline alumina support.

7. The method of claim 1, wherein the catalyst comprises a Ni and Sn and a crystalline alumina support.

8. The method of claim 1, wherein the support is a transitional alumina support.

9. The method of claim 8, wherein the support is a theta-alumina support.

10. The method of claim 3, wherein the catalyst comprises Pd, Mo, and Sn on a crystalline alumina support.

11. The method of claim 3, wherein the catalyst comprises a Ni and Sn and a crystalline alumina support.

12. The method of claim 3, wherein the support is a transitional alumina support.

13. The method of claim 12, wherein the support is a theta-alumina support.

* * * * *

UNITED STATES PATENT AND TRADEMARK OFFICE
CERTIFICATE OF CORRECTION

PATENT NO. : 9,695,094 B2  
APPLICATION NO. : 15/217715  
DATED : July 4, 2017  
INVENTOR(S) : Taylor Beck et al.

Page 1 of 1

It is certified that error appears in the above-identified patent and that said Letters Patent is hereby corrected as shown below:

In the Specification

Column 6, Line 58 - "$C_{4+}$" should be --$C_{1+}$--.

Column 39, Line 29 - "10000" should be --1000°--.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*